(12) United States Patent
Gmeiner et al.

(10) Patent No.: US 10,559,227 B2
(45) Date of Patent: Feb. 11, 2020

(54) SIMULATED TISSUE PRODUCTS AND METHODS

(71) Applicants: SYNAPTIVE MEDICAL (BARBADOS) INC., Bridgetown (BB); Timotheus Anton Gmeiner, Toronto (CA); Fergal Kerins, Toronto (CA); Gregory Allan Whitton, Toronto (CA); Kimberly Bojanowski Hoang, Toronto (CA)

(72) Inventors: Timotheus Anton Gmeiner, Toronto (CA); Fergal Kerins, Toronto (CA); Gregory Allan Whitton, Toronto (CA); Kimberly Bojanowski Hoang, Toronto (CA)

(73) Assignee: Synaptive Medical (Barbados) Inc., Bridgetown (BB)

(*) Notice: Subject to any disclaimer, the term of this patent is extended or adjusted under 35 U.S.C. 154(b) by 0 days.

(21) Appl. No.: 15/576,778

(22) PCT Filed: Jun. 2, 2016

(86) PCT No.: PCT/CA2016/050626
§ 371 (c)(1),
(2) Date: Nov. 24, 2017

(87) PCT Pub. No.: WO2017/173520
PCT Pub. Date: Oct. 12, 2017

(65) Prior Publication Data
US 2018/0308393 A1 Oct. 25, 2018

(30) Foreign Application Priority Data
Apr. 5, 2016 (WO) ................ PCT/CA2016/050389

(51) Int. Cl.
*G09B 23/30* (2006.01)
*G09B 23/28* (2006.01)
(Continued)

(52) U.S. Cl.
CPC .............. *G09B 23/30* (2013.01); *A61B 34/10* (2016.02); *B29C 35/02* (2013.01); *G09B 23/28* (2013.01);
(Continued)

(58) Field of Classification Search
CPC ......... C08L 29/04; A61L 27/52; G09B 23/28; G09B 23/306; G09B 23/30; A61B 34/10;
(Continued)

(56) References Cited

U.S. PATENT DOCUMENTS

| 4,198,766 A | 4/1980 | Camin |
| 4,663,358 A | 5/1987 | Hyon et al. |

(Continued)

FOREIGN PATENT DOCUMENTS

| CA | 2675217 | 2/2010 |
| WO | WO 021070980 | 9/2002 |
| WO | WO 2007/068050 | 6/2007 |

OTHER PUBLICATIONS

Chiellini et al., "Biodegradation of poly (vinyl alcohol) based materials", Nov. 12, 2002, Progress in Polymer Science, 28, p. 963-1014.*

(Continued)

*Primary Examiner* — Jack Yip
(74) *Attorney, Agent, or Firm* — Rowand LLP

(57) ABSTRACT

Simulated tissue products and methods involving an enhanced simulated tissue product, the enhanced simulated tissue product formed from a polyvinyl alcohol material having a molecular chain length in a range of at least approximately 7000 vinyl alcohol repeat units; and water, (Continued)

wherein the polyvinyl alcohol material has a preferred molecular chain length in a range of at least approximately 7150 vinyl alcohol repeat units; wherein the aqueous polyvinyl alcohol solution involves an additive, and, wherein the additive involves a plurality of nanoparticles. The simulated tissue products and methods are further useful with multimetric surgery simulator devices, systems, and methods, such as those for training surgical tasks.

16 Claims, 18 Drawing Sheets

(51) Int. Cl.
*A61B 34/10* (2016.01)
*B29C 35/02* (2006.01)
*A61B 34/20* (2016.01)
*A61B 17/11* (2006.01)
*B29K 29/00* (2006.01)
*B29L 31/00* (2006.01)

(52) U.S. Cl.
CPC ......... *A61B 17/11* (2013.01); *A61B 2034/105* (2016.02); *A61B 2034/2057* (2016.02); *B29K 2029/04* (2013.01); *B29L 2031/753* (2013.01)

(58) Field of Classification Search
CPC ...... A61B 2034/105; A61B 2034/2057; A61B 17/11; B29C 35/02; B29K 2029/04; B29L 2031/753
USPC ........................................................ 434/267
See application file for complete search history.

(56) References Cited

U.S. PATENT DOCUMENTS

| | | | |
|---|---|---|---|
| 4,789,340 A | 12/1988 | Zikria | |
| 4,894,013 A | 1/1990 | Smith et al. | |
| 4,974,461 A | 12/1990 | Smith et al. | |
| 5,792,809 A | 8/1998 | Nagao et al. | |
| 6,739,877 B2 | 5/2004 | Bailey et al. | |
| 6,918,771 B2 | 7/2005 | Arington et al. | |
| 7,455,523 B2 | 11/2008 | Hendrickson et al. | |
| 7,665,995 B2 | 2/2010 | Toly | |
| 7,857,626 B2 | 12/2010 | Toly | |
| 7,862,340 B2 | 1/2011 | Chen et al. | |
| 8,162,668 B2 | 4/2012 | Toly | |
| 8,323,029 B2 | 12/2012 | Toly | |
| 8,469,717 B2 | 6/2013 | Park et al. | |
| 8,556,635 B2 | 10/2013 | Toly | |
| 8,636,520 B2 | 1/2014 | Iwasaki et al. | |
| 9,105,200 B2 | 8/2015 | Chen et al. | |
| 9,202,389 B2 | 12/2015 | Okano | |
| 2002/0127525 A1 | 9/2002 | Arington et al. | |
| 2004/0009459 A1 | 1/2004 | Anderson et al. | |
| 2004/0126746 A1 | 7/2004 | Toly | |
| 2004/0161731 A1 | 8/2004 | Arington et al. | |
| 2004/0175684 A1 | 9/2004 | Kaasa et al. | |
| 2005/0048121 A1* | 3/2005 | East | A61K 9/0024 424/486 |
| 2005/0142525 A1 | 6/2005 | Cotin et al. | |
| 2005/0181342 A1 | 8/2005 | Toly | |
| 2005/0277096 A1 | 12/2005 | Hendrickson et al. | |
| 2006/0079597 A1 | 4/2006 | Muratoglu et al. | |
| 2006/0286524 A1 | 12/2006 | Boyers et al. | |
| 2007/0179621 A1* | 8/2007 | McClellan, III | A61F 2/442 623/17.16 |
| 2008/0076100 A1 | 3/2008 | Hendrickson et al. | |
| 2008/0187895 A1* | 8/2008 | Sakezles | G09B 23/306 434/268 |
| 2008/0208347 A1* | 8/2008 | Muratoglu | A61L 27/52 623/18.11 |
| 2009/0011394 A1 | 1/2009 | Meglan et al. | |
| 2009/0024181 A1 | 1/2009 | Raghavan et al. | |
| 2009/0068627 A1 | 3/2009 | Toly | |
| 2009/0111080 A1 | 4/2009 | Chen et al. | |
| 2011/0014596 A1 | 1/2011 | Kurenov et al. | |
| 2011/0117531 A1 | 5/2011 | Iwasaki et al. | |
| 2012/0034587 A1 | 2/2012 | Toly | |
| 2012/0045743 A1 | 2/2012 | Okano et al. | |
| 2012/0282584 A1* | 11/2012 | Millon | B29C 39/003 434/272 |
| 2012/0329904 A1 | 12/2012 | Suita et al. | |
| 2013/0085774 A1 | 4/2013 | Chen et al. | |
| 2013/0230837 A1 | 9/2013 | Meglan et al. | |
| 2014/0058009 A1* | 2/2014 | Choi | A61L 27/16 523/113 |
| 2014/0220527 A1 | 8/2014 | Li et al. | |
| 2014/0272863 A1 | 9/2014 | Kim | |
| 2014/0272866 A1 | 9/2014 | Kim | |
| 2014/0298886 A1* | 10/2014 | Nishi | A61B 5/0095 73/1.86 |
| 2014/0349265 A1 | 11/2014 | Park et al. | |
| 2014/0378573 A1 | 12/2014 | Suita et al. | |
| 2014/0378995 A1 | 12/2014 | Kumar et al. | |
| 2015/0054945 A1* | 2/2015 | Bangera | G01N 33/56911 348/135 |
| 2015/0086955 A1 | 3/2015 | Poniatowski et al. | |
| 2015/0140537 A1 | 5/2015 | Grinevich et al. | |
| 2015/0262511 A1 | 9/2015 | Lin et al. | |
| 2015/0347682 A1 | 12/2015 | Chen et al. | |

OTHER PUBLICATIONS

International Search Report dated Jan. 5, 2017, PCT Application No. PCT/CA2016/050389.
International Search Report dated Dec. 14, 2016, PCT Application No. PCT/CA2016/050626.

\* cited by examiner

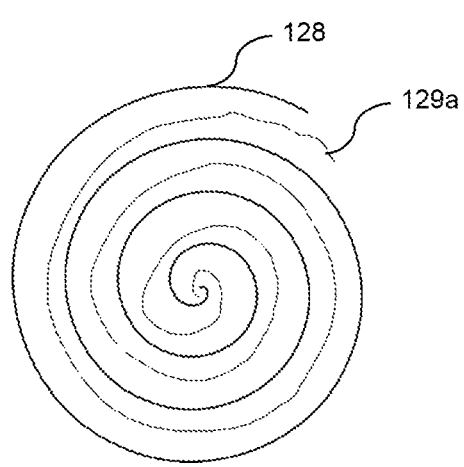 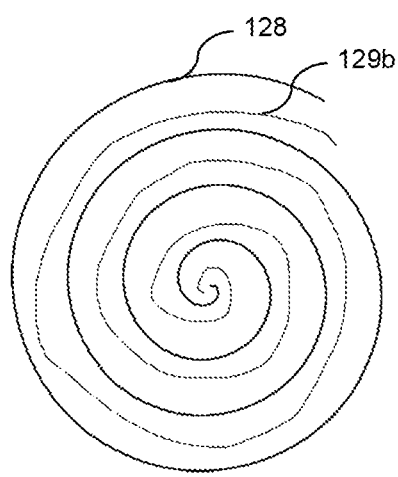
FIG. 6A FIG. 6B
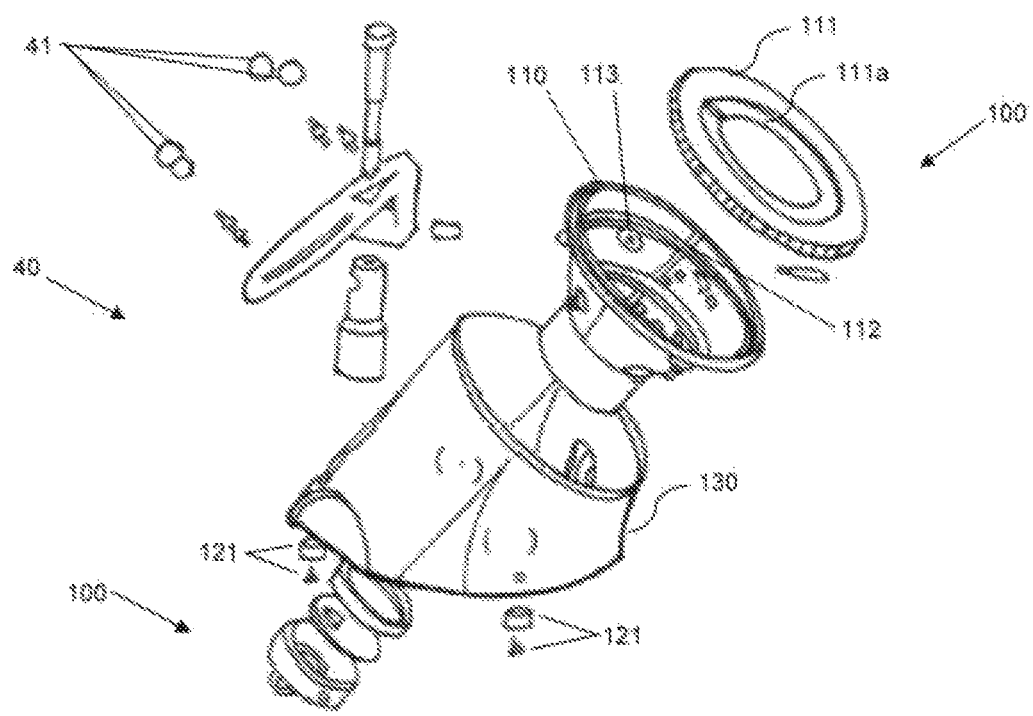
FIG. 7

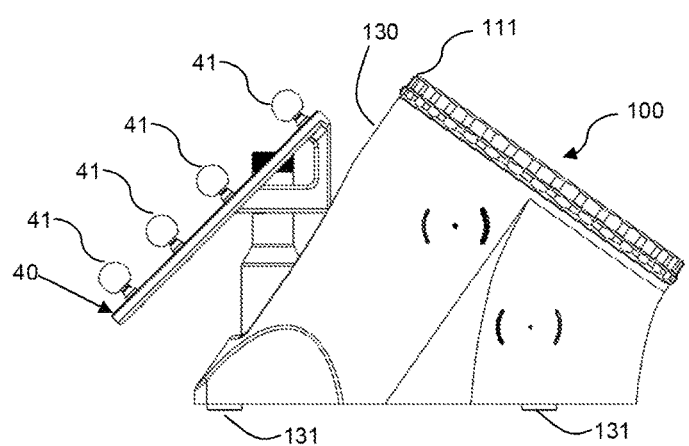
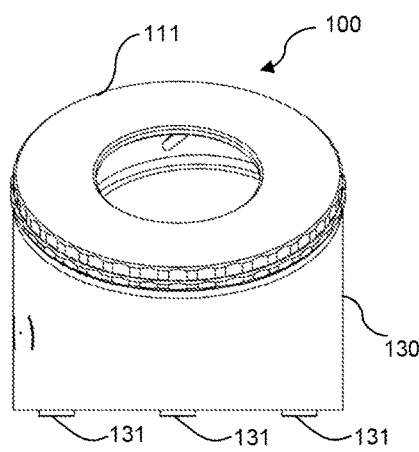
FIG. 8A          FIG. 8B
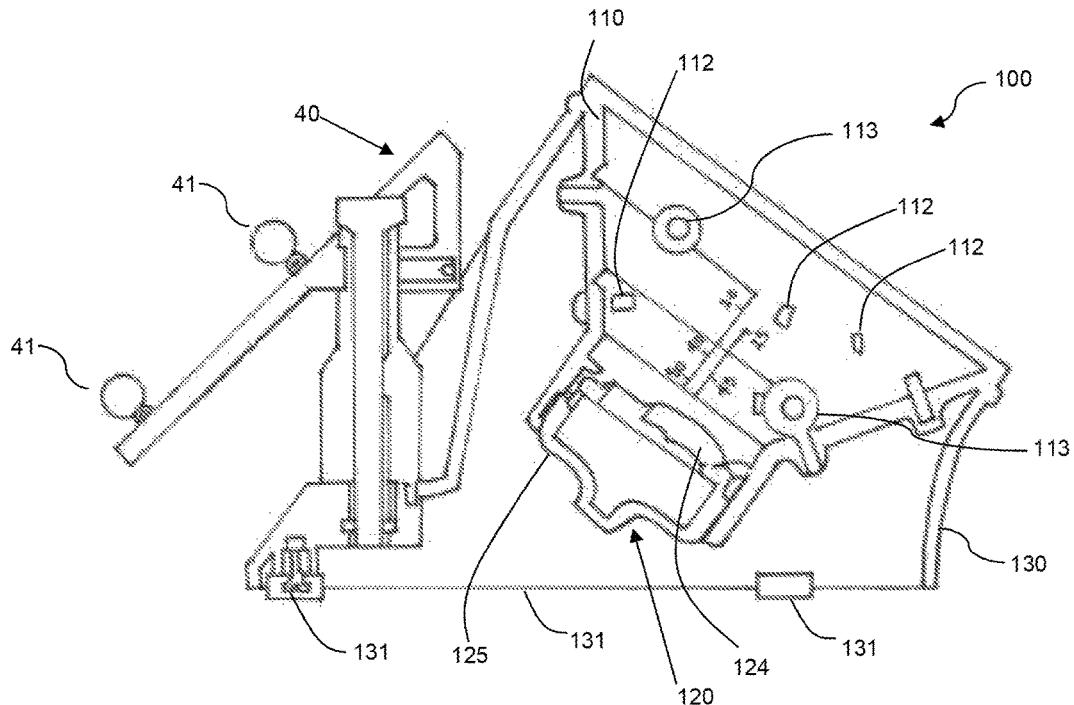
FIG. 9

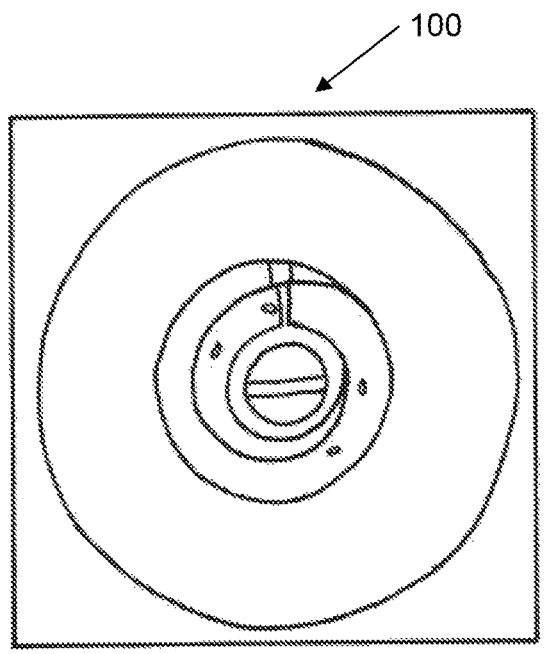 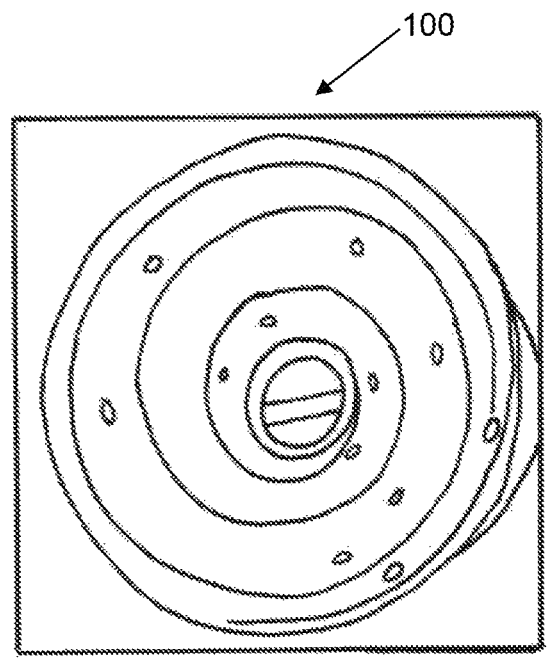
FIG. 22A          FIG. 22B
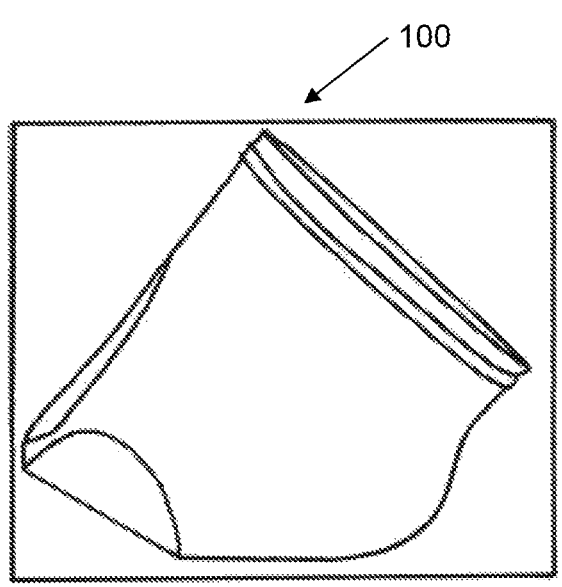 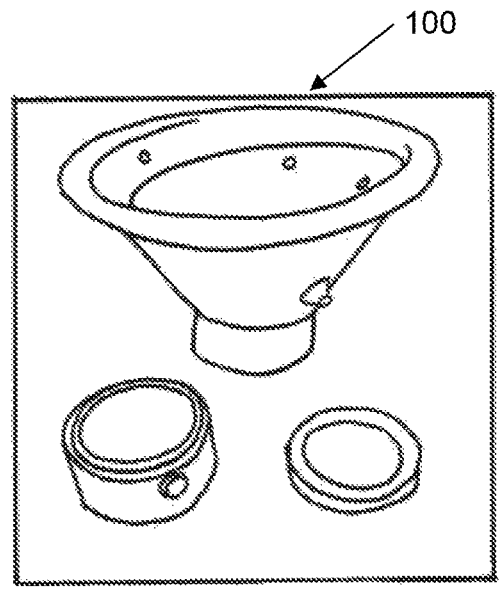
FIG. 22C          FIG. 22D

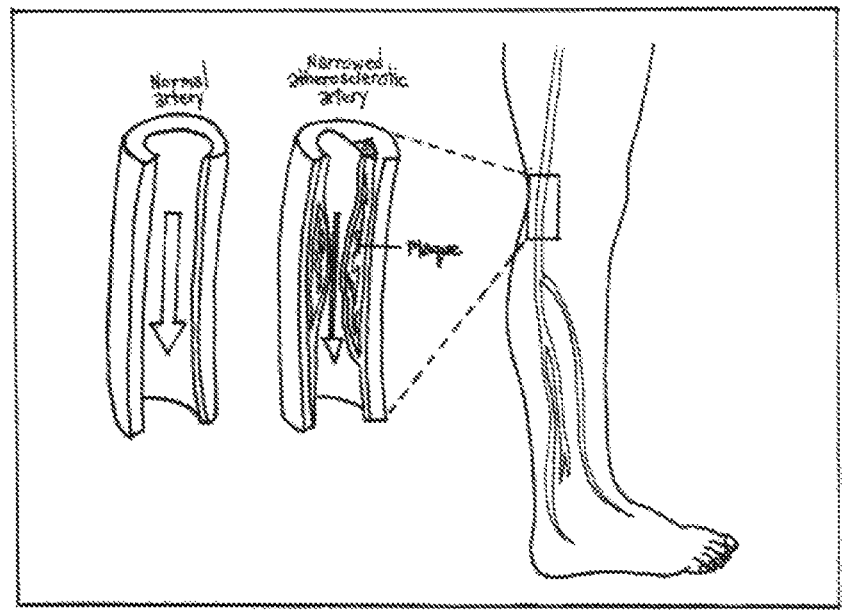
FIG. 23
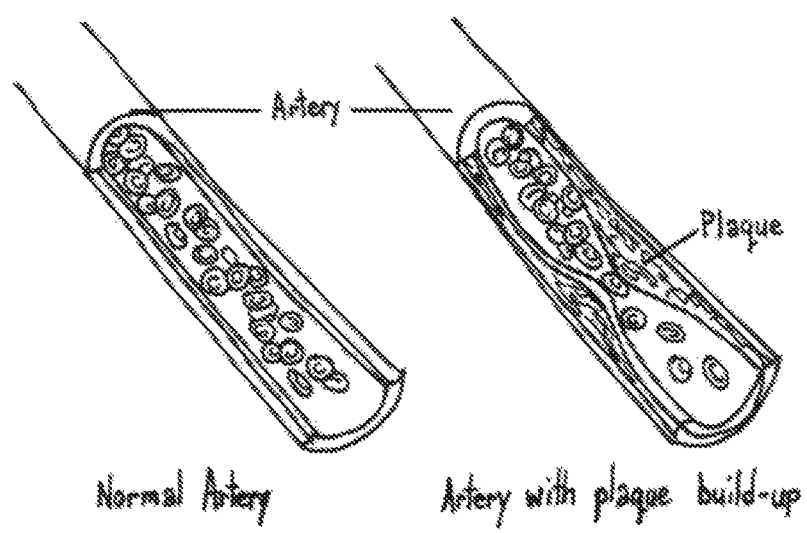
FIG. 24A                                  FIG. 24B

SIMULATED TISSUE PRODUCTS AND METHODS

CROSS-REFERENCE TO RELATED APPLICATION(S)

This document is a patent application which claims priority from international application PCT/CA2016/050389 filed on Apr. 5, 2016, entitled "MULTI-METRIC SURGERY SIMULATOR AND METHODS" which are hereby incorporated by reference in their entirety herein for all purposes.

TECHNICAL FIELD

The subject matter of the present disclosure generally relates to the field of tissue simulations for surgery simulators. More particularly, the subject matter of the present disclosure technically relates to the field of tissue simulations for surgery simulators in relation to image guided medical procedures. Even more particularly, the subject matter of the present disclosure technically relates to the field of tissue simulations for surgery simulators in relation to image guided medical procedures with surgical navigation.

BACKGROUND

In the related art, surgery, such as neurosurgery, for example, brain tumors are typically excised through an open craniotomy approach guided by imaging. The data collected in these solutions typically consists of computerized tomography (CT) scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, radiofrequency, or optical tracking devices. As a set, these devices are commonly referred to as surgical navigation systems and are often cumbersome and provide inaccurate tracking.

Port-based surgery is a minimally invasive surgical technique where a port is introduced to access a surgical region of interest using surgical tools. Unlike other minimally invasive techniques, such as laparoscopic techniques, a port diameter is larger than a tool diameter. Hence, the tissue region of interest is visible through the port, wherein exposed tissue in a region of interest, at a depth few centimetres below the skin surface, is accessible through a narrow corridor in the port.

Several related art problems generally preclude or impair the ability to perform port-based navigation in an intra-operative setting. For example, the position of the port axis relative to a typical tracking device (TD) is a free and uncontrolled parameter that prohibits the determination of access port orientation. Further, the limited access which is available, due to the required equipment for the procedure, causes indirect access port tracking to be impractical and unfeasible. Also, the requirement for angulation of the access port to access many areas within the brain during a procedure makes navigation of the access port a difficult and challenging problem that has not yet been addressed.

Additionally, the climbing costs of healthcare, coupled with alarming rates of malpractice suits, have highlighted the need for an efficient and effective method of surgical training in the related art, e.g., in relation to neurosurgery and cardiovascular surgery. Gross malpractice payments aside, surgical errors increase hospitalization time and adversely affect the health of patients, resulting in death or injury. The majority of these errors have been attributed to lack of skill and experience on the part of medical personnel. A number of simulation tools have been used in the related art, but have faced challenges in optimally training surgeons.

For instance, U.S. Patent Publication No. 20150347682 involves simulation by acquiring 2-D images, optionally including using X-rays, to generate 3-D or 4-D imaging. U.S. Patent Publication No. 20150347682 involves simulation by acquiring medical imaging data encoded in a standard video format. U.S. Patent Publication No. 20150086955 involves simulation of a tissue model configured so that one or more of the layers are in the form of a lattice structure rather than fully solid layers using silicone with 3-D printing. However, these related art tissue simulations are insufficiently realistic for optimally training surgeons.

In another example, U.S. Patent Publication No. 20140378995 involves a simulator having a surgeon's console with a software suite to simulate a surgical instrument and a training environment. This related art simulator has training exercises corresponding to difficulty levels, wherein, upon completion of a task, the user receives a report describing performance metrics and a composite score is calculated from these metrics in relation to only the user's own performance.

In addition, in the related art, phantoms or simulators are used in surgical training. Certain sub-anatomical features present a development manufacturing challenge in the related art. For example, brain ventricles are negative spaces within the brain that allow cerebral spinal fluid (CSF) to circulate and nourish the brain and provide protection against compression. A number of related art methods, e.g., as described in U.S. Pat. No. 9,202,389 to Okano (limited to simulated blood vessels), for preparing these structures have experienced many challenges, such as a related art method of creating voids or negative spaces, wherein balloons are inflated within a liquid hydrogel and subsequently cooled. After one freeze-thaw cycle (FTC), the balloon is removed from the hydrogel, whereby a scar is formed on the surface, thereby necessitating post-processing, such as back-filling with water and removal of air pockets that develop. Further, use of a polyvinyl alcohol (PVA) in the related art comprises using PVA having a molecular weight in a range of less than 3,500 vinyl alcohol units. Related art simulations also use silica particles for preventing stickiness of the low molecular weights PVA; however, the silica particles also impart an unrealistic texture to the simulation.

Another challenge in the related art involves the use of dimethyl sulfoxide (DMSO) as a solvent in formulated simulated tissue structures. However, the use of DMSO raises a number of safety concerns, such as toxicity and volatility. In terms of toxicity, although DMSO has been generally regarded as a non-toxic solvent with a median lethal dose higher than ethanol, harm to the eye, headaches, burning and itching of skin and strong allergic reactions have been experienced. Further, DMSO may cause contaminants, toxins, and medicines to be absorbed through the skin, with unexpected effects, such as acting as a developmental neurotoxin and causing genotoxicity, e.g., whereby the genetic infrastructure of cells is damaged, whereby mutations may be caused, and whereby cancer may develop. In terms of volatility, DMSO may be harmful if inhaled, causing respiratory tract infections. Furthermore, DMSO, as a solvent, has potentially damaging effects on contact with polymeric component parts in medical equipment, thereby leading to damage and loss of hardware as well.

Accordingly, challenges experienced in the related art include inaccuracy in training surgeons to perform neurosurgery or cardiovascular surgery, especially in relation to situations involving real-time registration of a surgical trajectory, wherein unique characteristics of a particular tissue types or sub-types, e.g., cerebral tissue or cardiovascular tissue, is significant. Also, surgical training involving simulated microvascular structures is particularly challenging for at least that realistic simulated microvascular strut cures are difficult to fabricate in the related art. For example, many related art simulated blood vessels are formed from silicone and rubber which have properties that are highly dissimilar to those of actual anatomic structures. Related art methods of training in anastomosis typically involve placing a simulated blood vessel in a flat disposition flat on a horizontal surface and performing a training task. Therefore, a need exists for improved simulated tissue products and methods that provide a realistic representation of anatomical structures without the use adverse fillers or adverse solvents for use with a surgery simulator.

BRIEF SUMMARY

In accordance with embodiments of the present disclosure, a variety of solutions address at least the related art challenges, by way of enhanced simulated tissue products and methods for improving accuracy and representation for anatomical models, e.g., for simulating blood vessels, microvascular structure, cerebral tissue, nerves, nerve fibers, nerve bundles, connective tissue, such as tendons, ligaments, and the like. The enhanced simulated tissue products and methods are operable with multi-metric devices, apparatuses, systems, and methods, e.g., involving a Clinical Skills Trainer (CST) CST which allows different degrees of difficulty and more realistic scenarios to be utilized. Such multi-metric devices, apparatuses, systems, and methods, when used in conjunction with the enhanced simulated tissue products and methods, provide improved feedback in relation to, not only the user's own performance, but also in relation to other users' performance, other statistical data, and ultimate performance goals, by way of a variety of metrics that include, but are not limited to, providing training in conjunction with surgical navigation systems for improving minimally invasive surgical procedures, such as an improved system and method for mapping navigation space to patient space modeling in relation to a given medical procedure, and providing modeling of the unique characteristics of a particular tissue types or sub-types, for example, cerebral tissue, as well as modeling of pathological tissue, wherein simulated tissue samples comprises a 3-D print or a rapid-prototype. By capturing the metrics of surgical training in relation to a variety of other metrics, as well as the user's metrics (multi-metric approach), data, and information, a surgeon's skill can be objectively evaluated in the embodiments of the present disclosure. The multi-metric devices, apparatuses, systems, and methods ensure that training sessions are more than just simulated "experiences" as multi-metric simulation provides a quantitatively validable clinical function. To date, such capabilities have been hitherto unknown in the related art.

In accordance with an embodiment of the present disclosure, an enhanced simulated tissue product comprises: a polyvinyl alcohol material having a molecular weight in a range of at least approximately 7000 vinyl alcohol units; and water. In a preferred embodiment, enhanced simulated tissue product comprises a polyvinyl alcohol material having a molecular weight in a range of at least approximately 7150+/−100 vinyl alcohol units, e.g., a higher molecular weight PVA than any related art formulation. In the formulations for the enhanced simulated tissue products of the present disclosure, adverse fillers, such as silica particles, and adverse solvent, such as DMSO, are eliminated. The enhanced simulated tissue product involves many embodiments, e.g., that simulate structures beyond vascularity, such as nerve bundles, and is configured to allow for testing standard surgical skills, facilitate training customization, and to provide consumable simulation products.

In accordance with another embodiment of the present disclosure, a method of fabricating an enhanced simulated tissue product comprises: providing an aqueous polyvinyl alcohol solution, providing the aqueous polyvinyl alcohol solution comprising providing a polyvinyl alcohol material having a molecular weight in a range of at least approximately 7000 vinyl alcohol units, providing water, and dissolving the polyvinyl alcohol material in the water; molding the aqueous polyvinyl alcohol solution; and iteratively temperature-cycling the aqueous polyvinyl alcohol solution, thereby providing the enhanced simulated tissue product.

In accordance with yet another embodiment of the present disclosure, a method of using an enhanced simulated tissue product operable with a multi-metric surgical simulator system comprises: providing the enhanced simulated tissue product operable with the multi-metric surgical simulator system, providing the enhanced simulated tissue product comprising providing an aqueous polyvinyl alcohol solution, providing the aqueous polyvinyl alcohol solution comprising providing a polyvinyl alcohol material having a molecular weight in a range of at least approximately 7000 vinyl alcohol units, providing water, and dissolving the polyvinyl alcohol material in the water; molding the aqueous polyvinyl alcohol solution; and iteratively temperature-cycling the aqueous polyvinyl alcohol solution, thereby providing the enhanced simulated tissue product; and commencing surgical training by way of the enhanced simulated tissue product operable with the multi-metric surgical simulator system.

Benefits of the multi-metric devices, apparatuses, systems, and methods, using a multi-metric performance characterization and operable with the enhanced tissue products and methods of the present disclosure, include, but are not limited to, establishing a benchmark level of proficiency for which a trainee must demonstrate at least competence, and preferably proficiency, before proceeding to further training. The multi-metric approach ensures that in graduating trainees have a homogeneous skill-set; and the multi-metric approach is applicable to any level of training and any surgical procedure as the multi-metric simulator devices, system, and methods are reconfigurable for a plurality of tools and sensing or tracking devices in relation to the tools for quantifying relevant training milestones. Prospective, randomized, and blind clinical studies relating to the multi-metric approach, using the enhanced simulated tissue products and methods of the present disclosure, have shown that trainees acquiring skills thereby perform significantly better in vivo as compared to traditionally trained colleagues using related art simulators.

Some of the features in the present disclosure are broadly outlined in order that the section entitled Detailed Description is better understood and that the present contribution to the art may be better appreciated. Additional features of the present disclosure are described hereinafter. In this respect, understood is that the present disclosure is not limited in its application to the details of the components or steps set forth herein or as illustrated in the several figures of the being carried out in various ways. Also, understood is that the phraseology and terminology employed herein are for the purpose of the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

FIG. 6A is a diagram illustrating a 2-D spiral training feature incorporable as an initial exercise feature and/or reconfigurable in relation to a simple surgical task portion as included in a surgery simulator apparatus of a multi-metric surgery simulator system, showing a user's tracing by way of a pen-tipped tool or stylus, by example only, in accordance with an embodiment of the present disclosure.

FIG. 6B is a diagram illustrating a 2-D spiral training feature incorporable as an initial exercise feature and/or reconfigurable in relation to a simple surgical task portion as included in a surgery simulator apparatus of a multi-metric surgery simulator system, showing another user's tracing by way of a pen-tipped tool or stylus, by example only, in accordance with an embodiment of the present disclosure.

FIG. 7 is a diagram illustrating an exploded perspective view of a surgery simulator apparatus of a multi-metric surgery simulator system, the surgery simulator apparatus comprising at least one of a simple surgical task portion and a complex surgical task portion, in accordance with an embodiment of the present disclosure.

FIG. 8A is a diagram illustrating a side view of a surgery simulator apparatus of a multi-metric surgery simulator system, as shown in FIG. 7, in accordance with an embodiment of the present disclosure.

FIG. 8B is a diagram illustrating a front view of a surgery simulator apparatus of a multi-metric surgery simulator system, as shown in FIG. 7, in accordance with an embodiment of the present disclosure.

FIG. 9 is a diagram illustrating a cross-sectional view of a surgery simulator apparatus of a multi-metric surgery simulator system, as shown in FIG. 7, in accordance with an embodiment of the present disclosure.

FIG. 22A is a diagram illustrating a top view of a surgery simulator apparatus, as shown in FIGS. 7-10, comprising a simple surgical task portion and complex surgical task portion, operable with the enhanced simulated tissue products and methods, in accordance with an embodiment of the present disclosure.

FIG. 22B is a diagram illustrating a top view of a surgery simulator apparatus, as shown in FIGS. 7-10, comprising a simple surgical task portion and complex surgical task portion, operable with the enhanced simulated tissue products and methods, in accordance with an embodiment of the present disclosure.

FIG. 22C is a diagram illustrating a side view of a surgery simulator apparatus, as shown in FIGS. 7-10, comprising a simple surgical task portion and complex surgical task portion, operable with the enhanced simulated tissue products and methods, in accordance with an embodiment of the present disclosure.

FIG. 22D is a diagram illustrating a side view of a surgery simulator apparatus, as shown in FIGS. 7-10, comprising a simple surgical task portion and complex surgical task portion, disassembled, operable with the enhanced simulated tissue products and methods, in accordance with an embodiment of the present disclosure.

FIG. 23 is a diagram illustrating a side internal perspective view of two conditions relating to vascular health, the two conditions comprising a normal artery condition (cut-away view) and a narrowed atherosclerotic arterial condition (cut-away view), wherein the enhanced simulated tissue product is configurable for facilitating surgical training, in accordance with an embodiment of the present disclosure.

FIG. 24A is a diagram illustrating a cut-away perspective view of a condition relating to vascular health, the condition comprising a normal artery condition (cut-away view), wherein the enhanced simulated tissue product is configurable for facilitating surgical training, such as for identifying healthy tissue, in accordance with an embodiment of the present disclosure.

FIG. 24B is a diagram illustrating a cut-away perspective view of a condition relating to vascular health, such as in relation to a human lea, by example only, the condition comprising a narrowed atherosclerotic arterial condition (cut-away view), wherein the enhanced simulated tissue product is configurable for facilitating surgical training, such as for identifying pathological tissue, in accordance with an embodiment of the present disclosure.

Figure 1:
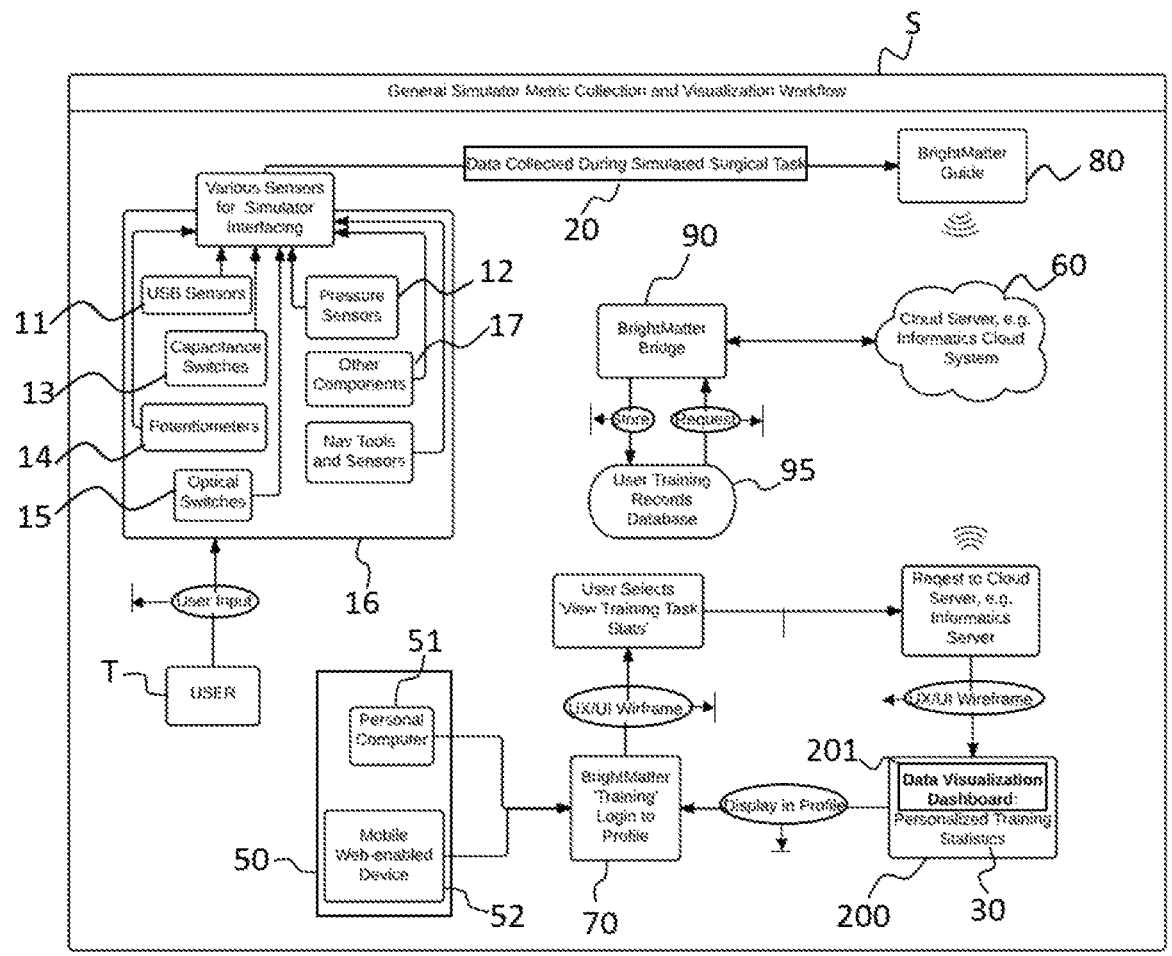
FIG. 1 is a schematic diagram illustrating a multi-metric surgery simulator system, comprising at least one of an clinical skills training apparatus and a Raman spectroscopic identification training apparatus, configured to perform at least one of multi-metric data collection and data visualization, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

The simulated tissue products and methods of the present disclosure are operable with the multi-metric simulator devices, apparatuses, systems, and methods and enhance the acquisition and maintenance of surgical skills in the realm of surgical training, wherein learning is optimized by way of the multi-metric feedback. The multi-metric feedback unambiguously characterizes a plurality of important aspects corresponding to each procedure of a plurality of surgical procedures. The multi-metric feedback is generated by analyzing each surgical task of each surgical procedure for a given training session or training curriculum. Further, the multi-metric simulator devices, system, and methods involve a self-reconfiguring feature, wherein the multi-metric feedback and/or the analysis related thereto also configure or reconfigure a given simulation in terms of visible presentation as well as function.

The subject matter described herein is useful in the field neurosurgery as well as the training thereof, including ontological care, neurodegenerative disease, stroke, brain trauma, spinal surgery, and orthopedic surgery. However, the subject matter of the present disclosure may extend or apply to other conditions or fields of medicine; and such extensions or applications are encompassed by the present disclosure. The systems and methods described herein encompass surgical processes that are applicable to surgical procedures for brain, spine, knee, and any other region of the body that will benefit from the use of an access port or small orifice to access the interior of an animal body, such as a human body.

Various systems, apparatuses, devices, or processes are below-described and provide examples of the navigation systems and methods embodiments, in accordance with embodiments of the present disclosure. None of the below-described embodiments limits any claimed embodiment; and any claimed embodiment may also encompass systems, apparatuses, devices, or processes which may differ from below-described examples. The claimed embodiments are not limited to systems, apparatuses, devices, or processes having all of the features of any one of the below-described systems, apparatuses, devices, or processes or to features common to some or all of the below-described systems, apparatuses, devices, or processes.

Furthermore, this Detailed Description sets forth numerous specific details in order to provide a thorough understanding of the various embodiments described throughout the present disclosure. However, understood is that the embodiments described herein may be practiced without these specific details. In other instances, conventional methods, procedures, and components have not been described in detail to prevent obscuring the embodiments of the present disclosure.

Referring to FIG. 1, this schematic diagram illustrates a multi-metric surgery simulator system S, operable with the enhanced simulated tissue products and methods, comprising at least one surgery simulator apparatus 100, the at least one surgery simulator apparatus 100 comprising at least one of an clinical skills training apparatus and a Raman spectroscopic identification training apparatus, the Raman spectroscopic identification training apparatus comprising a modular Raman training feature, configured to perform at least one of multi-metric data collection, whereby collected data 20 is obtainable, and data visualization, whereby a data visualization dashboard 200 is displayable, e.g., via a display device (not shown), in accordance with an embodiment of the present disclosure. The clinical skills training apparatus comprises a Clinical Skills Trainer (CST); and the Raman spectroscopic identification training apparatus comprising a modular Raman training feature, such as a Raman Spectroscopic Identification Trainer (RSIT). By using the CST, the multi-metric surgery simulator system S is configured to educate surgical trainees, further educate practicing neurosurgeons, and other healthcare professionals on the specific utility of the optics system, such as the Synaptive® Brightmatter™ guide system. The CST comprises a tabletop tool configured to operate with the Synaptive® Brightmatter™ navigation system 250, the Synaptive® Brightmatter™ drive system, and the Synaptive® Brightmatter™ optics systems for synergistically combining the features thereof.

Still referring to FIG. 1, a multi-metric surgery simulator system S, comprises: at least one sensor 10 configured to collect surgical training performance data relevant to at least one surgical task, the at least one sensor 10 configured to operate with a surgical navigation system, such as Synaptive® Brightmatter™ navigation system, comprising a processor, the processor configurable, by way of a set of executable instructions storable in relation to a non-transitory medium, to perform at least one of analyze collected data 20, transform the collected data 20, and provide feedback 30 in relation thereto; and at least one surgery simulator apparatus 100 operatively coupled with the at least one sensor 10, the at least one surgery simulator apparatus 100 configured to operate with a tracking system, such as the Synaptive®® Brightmatter™ guide system, whereby the collected data 20 is obtainable, and whereby clinical performance in relation to the at least one surgical task is quantitatively evaluable and progressively improvable, in accordance with an embodiment of the present disclosure.

Still referring to FIG. 1, the multi-metric surgery simulator system S further comprises a tracking feature 40 (FIGS. 7-10) coupled with the at least one surgery simulator apparatus 100 and configured to receive at least one signal from the at least one sensor 10 and to transmit at least one signal to the at least one processor (not shown), the tracking feature 40 comprising at least one of an optical tracking feature operable with a pointer tool and a Raman spectroscopic tracking feature operable with a Raman probe tool, e.g., the RSIT, by example only.

Still referring to FIG. 1, the processor (not shown) is further configured to transmit at least one of the collected data 20, the transformed collected data, and the feedback 30 to at least one of a user interface 50 and a storage medium. The user interface 50 is configured to provide access to at least one of the collected data 20, the transformed collected data, and the feedback 30 by at least one of at least one trainee T, at least one trainer (not shown), and at least one peer (not shown) via at least one of a server-based application, an Internet-based application, a cloud-based application, a mobile application, and a social media application.

Still referring to FIG. 1, the user interface 50 comprises a display device, such as a portable electronic device, e.g., a laptop 51 and a handheld device 52, e.g., a cellular phone and a smart phone. The storage medium comprises an informatics cloud, such as a non-transient memory device (not shown) and a cloud server, e.g., an informatics cloud server 60. The feedback 30 further comprises a plurality of feedback cycles, the plurality of feedback cycles comprising consultation information from at least one of the at least one trainer and the at least one peer after a training session, whereby convergent training is facilitated.

Still referring to FIG. 1, the at least one sensor 10 comprises at least one of at least one USB sensor 11, at least one pressure sensor 12, at least one capacitance switch 13, as least one potentiometer 14, at least one optical switch 15, at least one navigation tool sensor 16, and the like. The at least one surgery simulator apparatus 100 is further operable with a spectral biopsy probe (not shown), a broadband probe (not shown), a near-infrared probe (not shown), a fluorescent probe (not shown), a parallel imaging probe (not shown), a magnetic resonance imaging probe (not shown), a structured light scanning probe (not shown), and an augmented reality tool (not shown).

Still referring to FIG. 1, the processor is further configured to transmit information to the user interface, the information comprising: a prompt for a user's login information; a dashboard for facilitating visualization of data; a display of a user's profile; a display of a trainee's visuomotor training task statistics; a display of a trainee's training records; and a display of a trainee's current training session data in relation to at least one dataset of: initial threshold data relating to the surgical task, a trainee's past training session data, at least one other trainee's past training session data, and transformed threshold data relating to the surgical task, the transformed threshold data comprising an iterative computation relating to at least one of the initial threshold data relating to the surgical task, the trainee's past training session data, and the at least one other trainee's past training session data, wherein the at least one dataset comprises at least one parameter of a merit point, a demerit point, and a task completion time.

Still referring to FIG. 1, the multi-metric surgery simulator system S is configured to provide improved surgical fidelity in relation to a plurality of imaging tools or visualization tools, wherein surgical fidelity comprises the ability of a visualization tool to provide a trainee or a surgeon with visual input that results in the precise performance of a motor task in relation to initial exercise using basic endoscopes and basic microscopes, and in relation to subsequent exercises using the plurality of imaging tools. The multi-metric surgery simulator system S is configured to provide surgical training my way of a series of approximately six (6) exercises, by example only, whereby performance data is collected (collected data 20) and transformed in relation to a trainee or a surgeon. The collected data 20 is transformed for generating conclusions relating to surgical fidelity as a function of experience level and imaging tool type. The collected data 20 is transformed to generate the feedback 30, the feedback 30 comprising at least one demerit for inaccuracy in surgical tool positioning and a period of time for completion of each respective surgical task.

Still referring to FIG. 1, the feedback 30 further facilitates development of surgical skills by providing information to a user relating to visuomotor skills for surgical accuracy improvement over time regarding a trainee or a surgeon and by providing information to a user relating to the manner in which the skill improvement differs regarding a trainee or a surgeon, e.g., in relation to the trainee or surgeon, in relation to other trainees or surgeons, and/or in relation to historical data from at least one database. The feedback 30 further facilitates updating of planned trajectories, e.g., during an actual surgical procedure as well as a simulation thereof. The multi-metric surgery simulator system S, being configured to provide improved surgical fidelity in relation to a plurality of imaging tools, improves a trainee's or a surgeon's ability to use indirect cues, such as motion parallax, relative size of structures, in-and-out movements, familiarity with image distortion, and the like, to compensate for lack of true three-dimensional perception, thereby decreasing learning curves.

Still referring to FIG. 1, the multi-metric simulator devices, apparatuses, and systems, are configurable and/or reconfigurable for a specific medical or surgical procedure. The mufti-metric simulator system S comprises sensors 10 that collect data relevant to specific tasks being performed by a surgical trainee, such as the trainee T. The collected data 20 are stored, e.g., in cloud storage, such as via a Synaptive® system's informatics-cloud; and feedback based on the collected data 20 is visible (displayable) to a user, e.g., a trainee T and/or other relevant party at his/her convenience. After a training session, through feedback 30 from the Synaptive® system's ecosystem during a training session, reference to a user's training performance data, and consultation with at least one of at least one trainer and at least one peer, a trainee T experiences significantly more feedback cycles relating to his/her training than provided by related art simulators. By coupling this type of infrastructure with Synaptive® surgical simulators, e.g., the system S, of various kinds, e.g., using Synaptive® surgical navigation systems, Synaptive® tracking systems, and the like, the trainee T would be able to see progressive improvement in key visuomotor skills before in vivo skill testing and at significantly more convenience and lower cost than by using cadavers.

Still referring to FIG. 1, the multi-metric simulator system S of the present disclosure is used as a skill development tool for training surgeons and obtaining quantitative metrics on their progress in conjunction with a Synaptive® technology suite, whereby the multi-metric simulator system S is configured to link thereto via the Synaptive® Brightmatter™ Guide 80 to the Synaptive® Brightmatter™ Bridge 90 for facilitating storing performance data in a database 95, e.g., a web-app-accessible database. This linking feature enables users, training centers, and clinical administrators to log-in, evaluate, and share performance statistics for better understanding as to the manner in which a trainee's performance compares with a trainee's previous performance as well as with peers or to historical averages, whereby social components are incorporable into the multi-metric simulator system S, e.g., via competition features and prize features to motivate surgical residents to strive for the utmost in surgical proficiency.

Still referring to FIG. 1, the multi-metric simulator system S of the present disclosure is configured to demonstrate other Synaptive® hardware/software and could scale for integration with magnetic resonance (MR), combined Raman Spectroscopy (RS) and Optical Coherence Tomography (OCT) ("Raman-OCT"), and a myriad of other current and future devices. The datasets generated by the multi-metric simulator system S are useable for collecting historical statistical data on how surgeons use our tool which could aid in verification and validation (V&V) activities, generation marketing, the manner in which a surgeon's performance is improvable by reconfiguration or self-reconfiguration of the multi-metric simulator system via additional product variables, e.g., feature offerings, that are identifiable via operation of the multi-metric simulator system. The multi-metric simulator devices, apparatuses, systems, and methods of the present disclosure encompass general workflow application, wherein the multi-metric simulator apparatus comprises at least one of a Clinical Skills Trainer (CST) and a Raman Spectroscopic Identification Trainer (RSIT).

Figure 2:
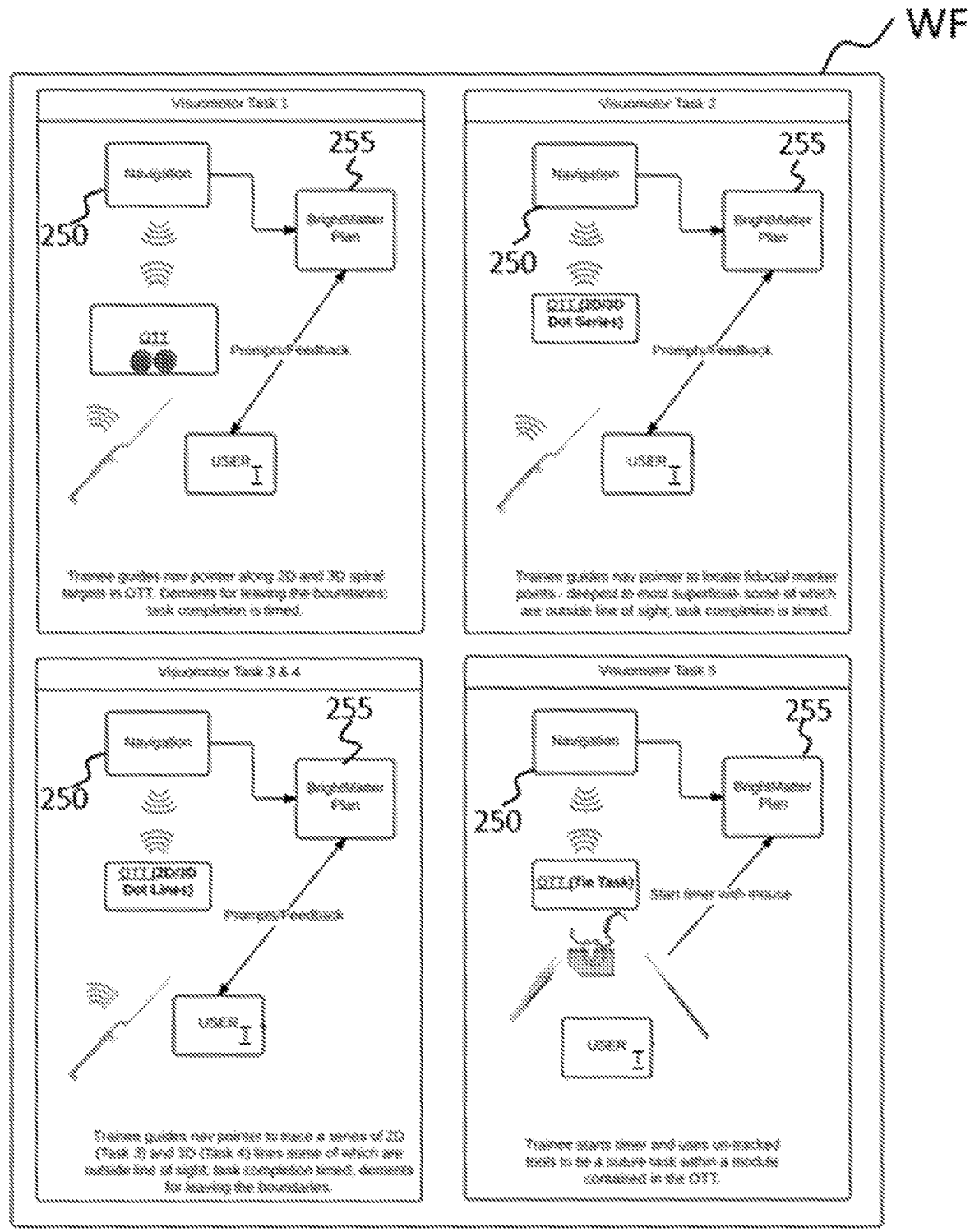
FIG. 2 is a schematic diagram illustrating workflow relating to five visuomotor tasks related to a given surgical procedure in relation to an clinical skills training apparatus, by example only, in accordance with an embodiment of the present disclosure.

Referring to FIG. 2, this schematic diagram illustrates workflow WF relating to five visuomotor tasks related to a given surgical procedure in relation to a surgery simulator apparatus 100, operable with the enhanced simulated tissue products and methods, comprising a clinical skills training apparatus having an optical tracking feature, by example only, in accordance with an embodiment of the present disclosure. For a surgery simulator apparatus 100 comprising a clinical skills clinical skills training apparatus having an optical tracking feature, the at least one surgical task comprises at least one training routine of a spiral target routine (FIGS. 6A and 6B), a fiducial marker point routine, a blind target routine, and a suturing routine (FIG. 14), by example only. The clinical skills training apparatus, having an optical tracking feature, is iteratively operable in relation to one through five of five tasks for generating two performance datasets, e.g., indicating total demerit points and task completion time, in accordance with an embodiment of the present disclosure. The clinical skills training apparatus CST is configured to communicate with navigation system 250; and the navigation system 250 is configured to communicate with a planning system 255.

Still referring to FIG. 2 and ahead to FIGS. 15-17, by example only, the workflow WF relating to five visuomotor tasks comprises a first simple visuomotor task (Visuomotor Task 1), the first simple visuomotor task comprising: guiding or tracing, using a tool with a pen tip, along a 2-D spiral path of the 2-D spiral training feature 128; and observing the tracing via a microscope and subsequently an endoscope, wherein a demerit point is assigned for each instance that the tracing overlaps a designated boundary region of the 2-D spiral training feature 128, e.g., a darkened area, and wherein the number of demerit points is inversely related to a performance score, wherein a time period for completion of a surgical task is measured and recorded, and wherein the time period is inversely related to the performance score, and guiding (or tracing) (line series) a tool with a pen tip along a 3-D spiral path of the 3-D spiral training feature 128'; and observing the tracing via a microscope and subsequently an endoscope, wherein a demerit point is assigned for each instance that the tracing overlaps a designated boundary region of the 3-D spiral training feature 128', e.g., a darkened area, wherein the number of demerit points is inversely related to a performance score, wherein a time period for completion of a surgical task is measured and recorded, and wherein the time period is inversely related to the performance score.

Figure 15:
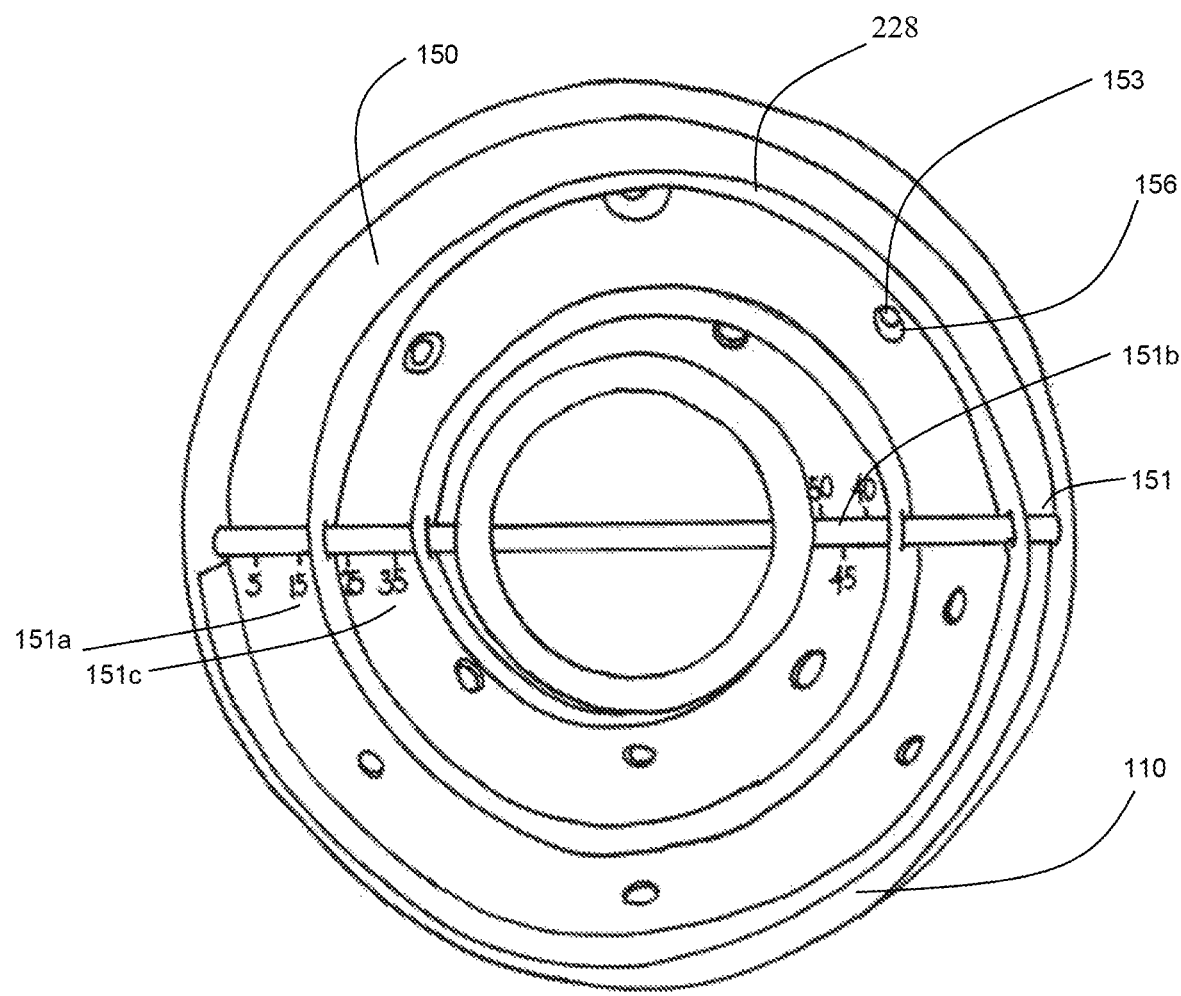
FIG. 15 is a diagram illustrating a top view of a simple surgical task portion comprising at least one of a 3-D spiral training feature, as included in a multi-metric surgery apparatus of a multi-metric surgery simulator system, in accordance with an embodiment of the present disclosure.
Figure 16:
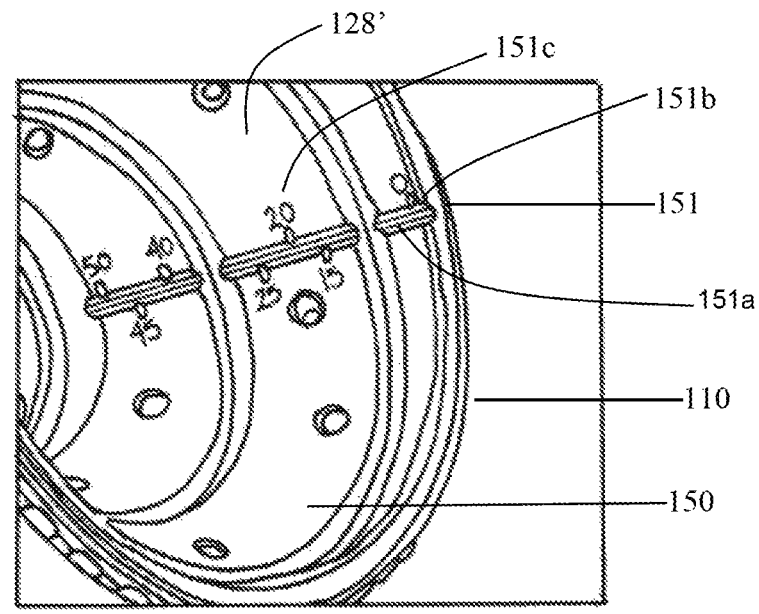
FIG. 16 is a diagram illustrating a top view of a simple surgical task portion comprising at least one of a 3-D spiral training feature, as included in a multi-metric surgery apparatus of a multi-metric surgery simulator system, in accordance with an embodiment of the present disclosure.
Figure 17:
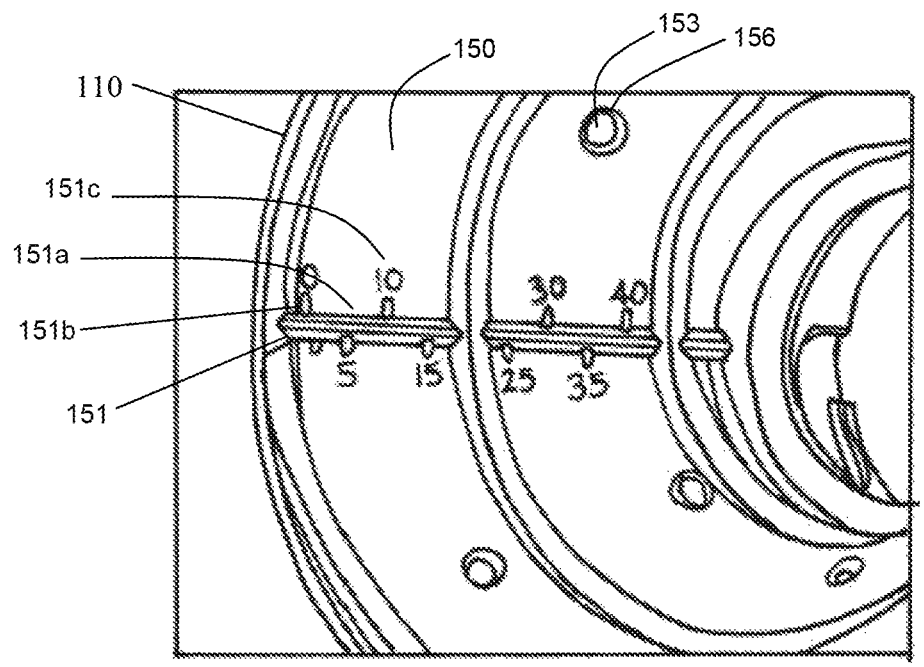
FIG. 17 is a diagram illustrating an alternative cut-away interior perspective view of a simple surgical task portion comprising at least one of a 3-D spiral training feature, as included in a multi-metric surgery apparatus of a multi-metric surgery simulator system, in accordance with an embodiment of the present disclosure.

Still referring to FIG. 2 and ahead to FIGS. 15-17, by example only, the workflow WF relating to five visuomotor tasks further comprises a second simple visuomotor task (Visuomotor Task 2), the second simple visuomotor task comprising: guiding or tracing a tool with a pen tip to locate a plurality of fiducial markers, wherein a portion of the plurality of fiducial markers are disposed deeper than another portion of fiducial markers, wherein at least a portion of the fiducial markers are disposed away from the trainee line of sight, wherein a demerit point is assigned for each instance that the tracing fails to coincide with fiducial markers, wherein the number of demerit points is inversely related to a performance score, and wherein a time period for completion of the second simple visuomotor task is measured and recorded.

Still referring to FIG. 2 and ahead to FIGS. 15-17, by example only, the workflow WF relating to five visuomotor tasks further comprises: a third simple visuomotor task (Visuomotor Task 3), the third simple visuomotor task comprising: guiding or tracing, using a tool with a pen tip, to locate a plurality 2-D, wherein at least a portion of the plurality 2-D lines are disposed away from the trainee line of sight, wherein a demerit point is assigned for each instance that the tracing fails to coincide with the 2-D lines, and wherein a time period for completion of the third simple visuomotor task is measured and recorded; and a fourth simple visuomotor task (Visuomotor Task 4), the fourth simple visuomotor task comprising: guiding or tracing, using a tool with a pen tip, to locate a plurality 3-D, wherein at least a portion of the plurality 3-D lines are disposed away from the trainee line of sight, wherein a demerit point is assigned for each instance that the tracing fails to coincide with the 3-D lines, and wherein a time period for completion of the fourth simple visuomotor task is measured and recorded.

Still referring to FIG. 2 and ahead to FIGS. 15-17, by example only, the workflow WF relating to five visuomotor tasks further comprises: a fifth simple visuomotor task (Visuomotor Task 5), the fifth simple visuomotor task comprising: performing suturing exercises, using an untracked tool around two small parallel pillars disposed in a perpendicular orientation relative to the trainee's line of sight, wherein at least a portion of the plurality 2-D lines are disposed away from the trainee line of sight, wherein a time period for completion of the third simple visuomotor task is measured and recorded.

Figure 3:
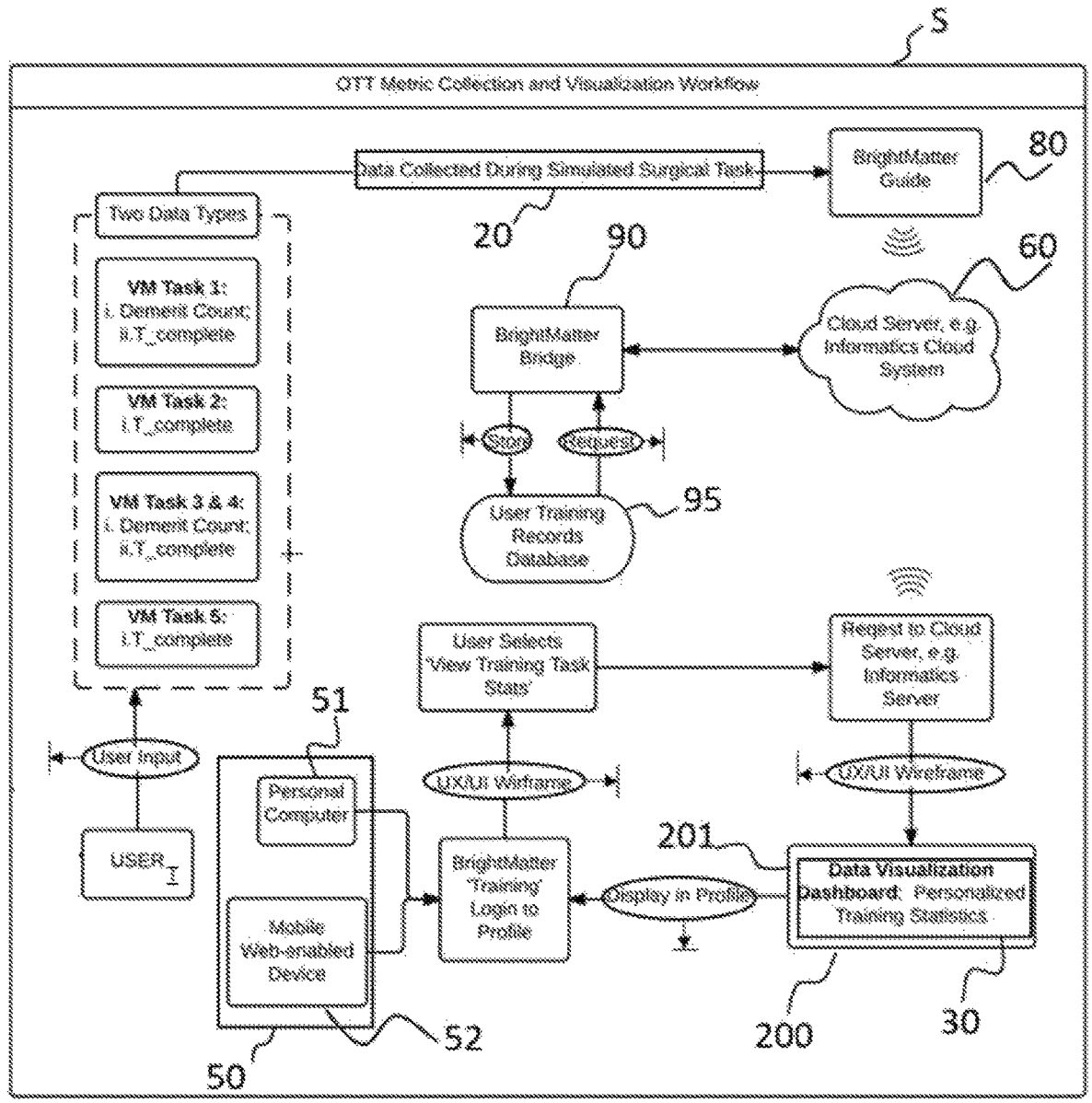
FIG. 3 is a schematic diagram illustrating a multi-metric surgery simulator system, comprising an clinical skills training apparatus, as shown in FIG. 2, configured to perform at least one of multi-metric data collection and data visualization, in accordance with an embodiment of the present disclosure.

Referring to FIG. 3, this schematic diagram illustrates a multi-metric surgery simulator system S, comprising a surgery simulator apparatus 100, operable with the enhanced simulated tissue products and methods, comprising a clinical skills training apparatus having an optical tracking feature, as shown in FIG. 2, configured to perform at least one of multi-metric data collection and data visualization, in accordance with an embodiment of the present disclosure. By using the optical tracking feature, such as the CST, a merit point is determined for the pointer tool moved within a predetermined boundary, a demerit point is determined for the pointer tool moved outside the predetermined boundary, and a task completion time is determined for each at least one training routine, by example only.

Figure 4:
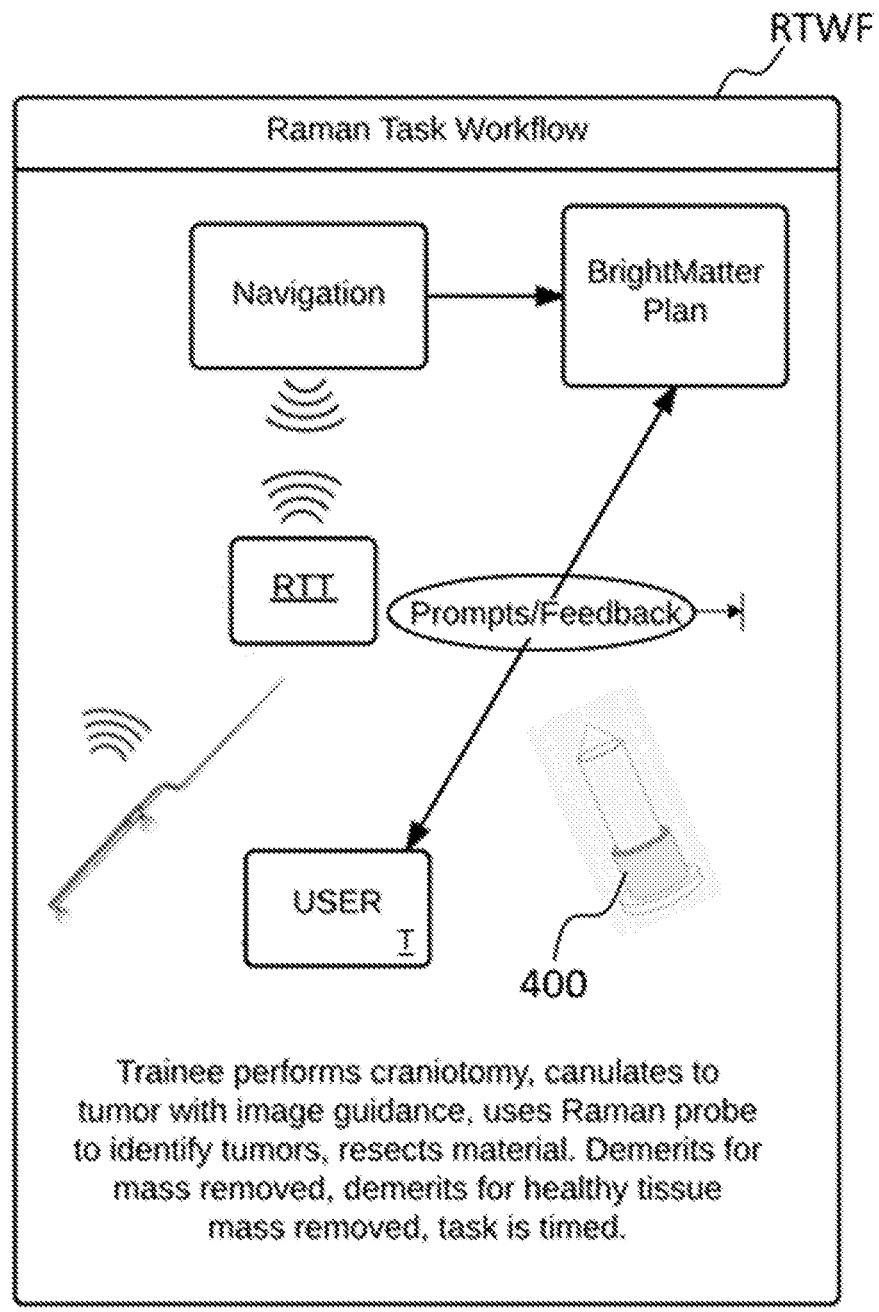
FIG. 4 is a schematic diagram illustrating workflow relating to three visuomotor tasks, such as a craniotomy, a cannulation, and a resection, related to a given surgical procedure in relation to a Raman spectroscopic identification training apparatus, by example only, in accordance with an embodiment of the present disclosure.

Referring to FIG. 4, this schematic diagram illustrates Raman task workflow RTWF relating to three visuomotor tasks, such as a craniotomy, a cannulation, and a resection, related to a given surgical procedure in relation to a surgery simulator apparatus 100, as included in a multi-metric surgery simulator system S, operable with the enhanced simulated tissue products and methods, comprising a Raman spectroscopic identification training apparatus having a Raman spectroscopic identification feature, e.g., a Raman task trainer RTT, by example only, in accordance with an embodiment of the present disclosure. By using the Raman spectroscopic tracking feature, the at least one surgical task comprises at least one of incision, craniotomy, cannulation, resection, transplantation, suturing, decannulating, and closing for each data type, such as data relating to the mass of removed simulated tour, the mass of removed simulated healthy tissue, and the duration for task completion (FIG. 5).

Still referring to FIG. 4, the surgery simulator apparatus 100, as included in a multi-metric surgery simulator system S, comprising a Raman spectroscopic identification training apparatus having a Raman spectroscopic identification feature comprises surface-enhanced Raman scattering (SERS) nanoparticles configured to generate distinct spectra and are potentially useful as bright contrast agents for molecular diagnostics, in accordance with an embodiment of the present disclosure. Similarly, large volume liquid tissue "phantoms" that simulate breast and prostate cancerous tissue for Raman identification have been made using an intralipid (scattering agent), Indian ink (absorption agent), and synthesized calcification powder (calcium hydroxyapatite) and are encompassed by the present disclosure. The system S is configured as a Raman tissue simulator to accommodate a large volume tissue "phantom" or simulated tumour inserts, e.g., simulated cancerous tissue inserts, that contain elements that are responsive to Raman spectroscopy tools in a manner that is quantitatively evaluable.

Still referring to FIG. 4, the simulated tissue, e.g., a PVA-hydrogel doped with surface-enhanced Raman spectroscopy (SERS) nanoparticles, such as in the form of simulated brain tissue, is modeled to incorporate simulated imbedded tumor targets comprising Raman-spectroscopy-tunable and responsive to a Raman spectroscopy instrument, such as a spectroscopy probe 400, wherein the simulated brain tissue is cannulable, having an identifiable spectra, inspectable with the Raman-probe, and resectable. For example, the surgery simulator apparatus 100, comprising a Raman spectroscopic identification training apparatus having a Raman spectroscopic identification feature, e.g., a Raman task trainer RTT. The SERS nanoparticles comprise any nanoparticle that is suitable for a surface-sensitive technique that enhances Raman scattering by molecules adsorbed on rough metal surfaces or by nanostructures, such as plasmonic-magnetic nanotubes and the like. The enhancement factor comprises a range of approximately 1010 to approximately 1011, wherein a single molecule is detectable.

Figure 5:
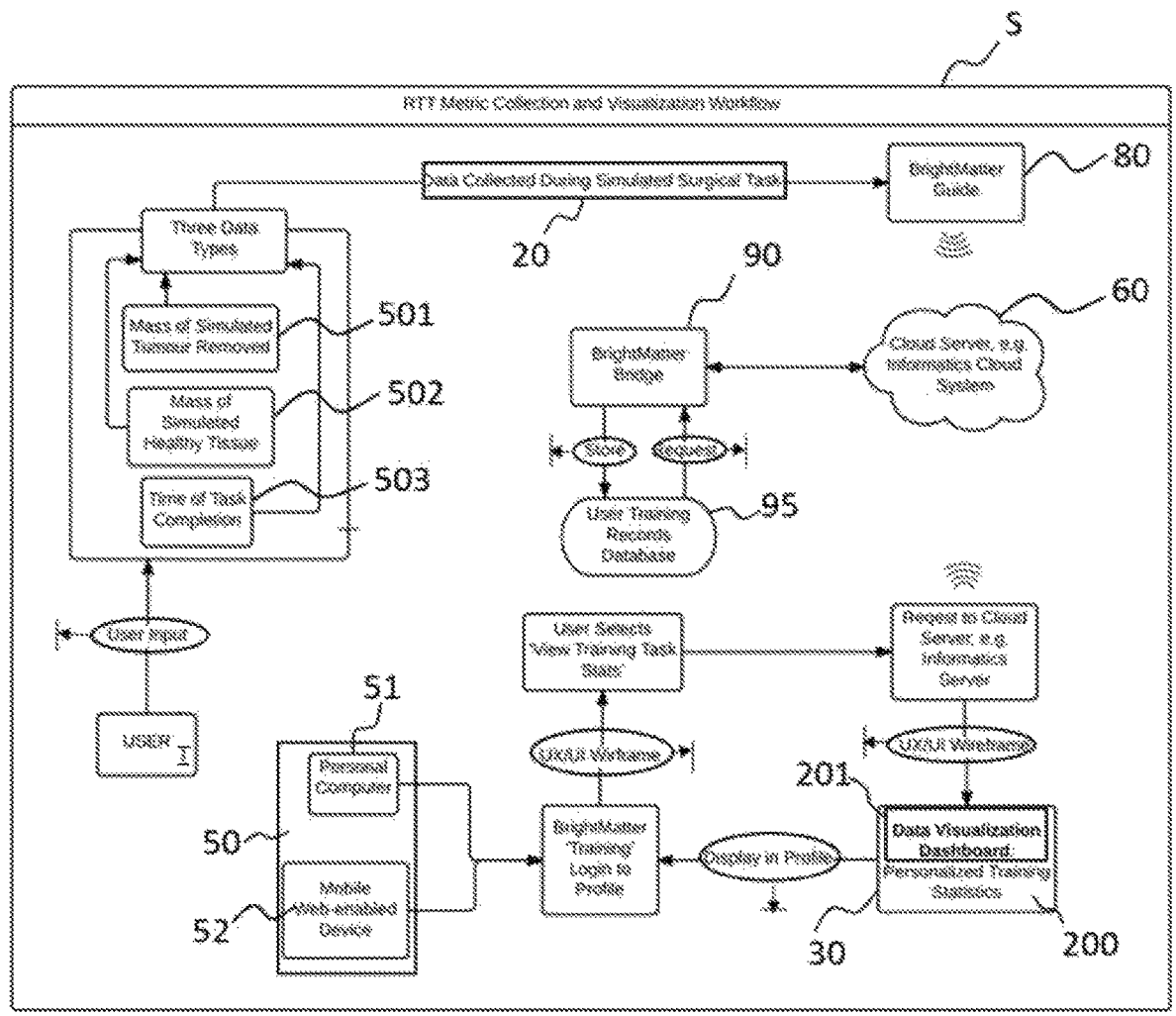
FIG. 5 is a schematic diagram illustrating a multi-metric surgery simulator system, comprising Raman spectroscopic identification training apparatus, as shown in FIG. 4, configured to perform at least one of multi-metric data collection and data visualization, in accordance with an embodiment of the present disclosure.

Referring to FIG. 5, this schematic diagram illustrates a multi-metric surgery simulator system S comprising a surgery simulator apparatus 100, operable with the enhanced simulated tissue products and methods, the surgery simulator apparatus 100, operable with the enhanced simulated tissue products and methods, comprising a Raman spectroscopic identification training apparatus having a Raman spectroscopic identification feature, e.g., a Raman task trainer RTT, as shown in FIG. 4, configured to perform at least one of multi-metric data collection and data visualization, in accordance with an embodiment of the present disclosure. For surgery simulator apparatus 100, comprising the Raman spectroscopic tracking feature, for each at least one surgical task, a merit point is determined for resection of the at least one simulated pathological tissue feature by using data 501 collected in relation to the mass of the simulated pathological tissue feature, e.g., a simulated tumour, a demerit point is determined for resection of any portion of the at least one simulated healthy tissue feature by using data 502 collected in relation to the mass of the simulated healthy tissue feature, and a task completion time is determined by using data 503 collected in relation thereto. As such, three types of data 500 are collected and transmitted as collected data 20 to the guidance system, such as the Synaptive® Brightmatter™ guidance system 80.

Still referring to FIG. 5, the surgery simulator apparatus 100 comprises a Raman spectroscopic identification training apparatus having a Raman spectroscopic identification feature, e.g., a Raman task trainer RTT. The system S, comprising the surgery simulator apparatus 100, is compatible with any data-generating input and is linkable to any and all Synaptive® hardware, firmware, or software tools and incorporable in relations to a plurality of training simulation programs. For example, the system S is linkable to at least the following tools or equipment: the Synaptive® Spectral Biopsy Probe, the Synaptive® Spectroscopy Probe (broadband, NIR, Raman, Fluorescence, etc.), the Synaptive® parallel imaging probe, MRI equipment, structured light scanning equipment, the Synaptive® Mixed-Medical Reality hardware/software tools, the Synaptive® laser-ablation phantom, the Synaptive® Hematoma Task Trainer Phantom, the Synaptive® tumor resection phantom, the Synaptive® deep brain stimulation phantom, the Synaptive® endonasal procedure phantom, the Synaptive® lower lumbar procedure phantom, the Synaptive® orthopedic procedure phantom, and the like. In the embodiments of the present disclosure, the collected data is transformed for providing feedback comprising key surgical performance indicators, wherein the system S is reconfigurable and scalable for simulating and training any medical device-coupled procedure.

Referring to FIG. 6A, this diagram illustrates a 2-D spiral training feature 128 incorporable as an initial exercise feature and/or in relation to an upper surface 111a of a simple surgical task portion fastener 111 for the simple surgical task portion 110 (FIG. 7), as included in a surgery simulator apparatus 100 of a multi-metric surgery simulator system S, operable with the enhanced simulated tissue products and methods, showing a user's tracing 129a by way of a pen-tipped tool (not shown) or stylus (not shown), by example only, in accordance with an embodiment of the present disclosure. Initially, training may commence with a simple visuomotor task performed under a microscope and subsequently performed via an endoscope. For example, a first simple visuomotor task comprises guiding (or tracing) (line series) a tool with a pen tip along a 2-D spiral path of the 2-D spiral training feature 128; and observing the tracing via a microscope and subsequently an endoscope, wherein a demerit point is assigned for each instance that the tracing overlaps a designated boundary region of the 2-D spiral training feature 128, e.g., a darkened area, and wherein the number of demerit points is inversely related to a performance score, wherein a time period for completion of a surgical task is measured and recorded, and wherein the time period is inversely related to the performance score.

Referring to FIG. 6B, this diagram illustrates a 2-D spiral training feature 128 incorporable as an initial exercise feature and/or in relation to an upper surface 111a of a simple surgical task portion fastener 111 for the simple surgical task portion 110 (FIG. 7), as included in a surgery simulator apparatus 100 of a multi-metric surgery simulator system S, operable with the enhanced simulated tissue products and methods, showing another user's tracing 129b by way of a pen-tipped tool (not shown) or stylus (not shown), by example only, in accordance with an embodiment of the present disclosure. Initially, training may commence with a simple visuomotor task performed under a microscope and subsequently performed via an endoscope. For example, a first simple visuomotor task comprises guiding (or tracing) a tool with a pen tip along a 2-D spiral path; and observing the tracing via a microscope and subsequently an endoscope, wherein a demerit point is assigned for each instance that the tracing overlaps a designated boundary region of the 2-D spiral training feature 128, e.g., a darkened area, and wherein the number of demerit points is inversely related to a performance score, wherein a time period for completion of a surgical task is measured and recorded, and wherein the time period is inversely related to the performance score.

Still referring to FIG. 6B and referring back to FIG. 6A, the 2-D spiral training feature 128 is incorporable in relation to the upper surface 111a of a simple surgical task portion fastener 111 for the simple surgical task portion 110 (FIG. 7) is configured to support at least one of at least one surgical task pattern (not shown) and at least one simulated tissue feature (not shown). The 2-D spiral training feature 128 may be modular and disposable within a recessed portion of the upper surface 111a. In the example shown in FIG. 6A, the at least one surgical task pattern optionally comprises a spiral configuration and may be incorporated into a modular member for coupling with the simple surgical task portion 110, such as by way of at least one clipping feature, by example only. Further, the at least one surgical task pattern comprises a modification of the 2-D spiral training feature 128 to provide a third dimension, e.g., depth, wherein the at least one surgical task pattern comprises a 3-D spiral training feature 128' configured to couple with the simple surgical task portion 110, as included in a surgery simulator apparatus 100 of a multi-metric surgery simulator system S, and provides training for following a surgical trajectory, such as would be defined by a surgical plan, e.g., for training an access port procedure. The 3-D spiral training feature 128' comprises a generally funnel shape (FIGS. 15-17) for disposition within the simple surgical task portion 110.

Figure 14:
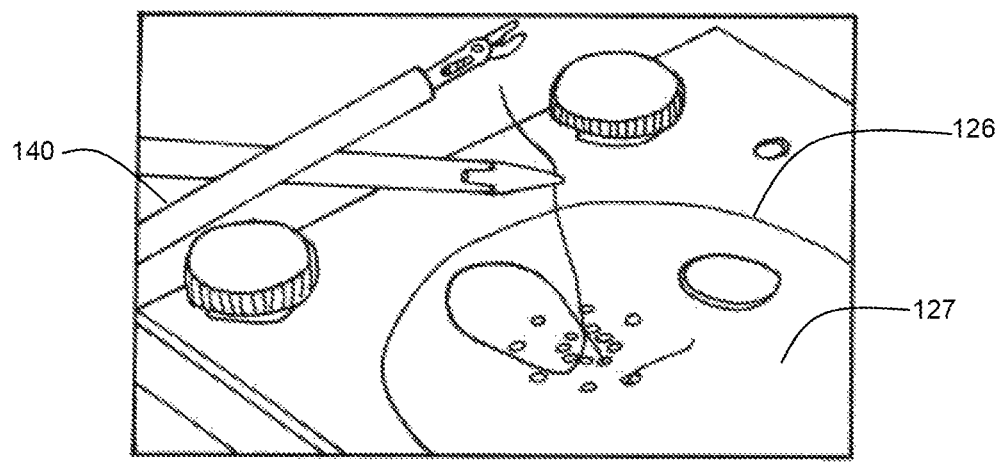
FIG. 14 is a diagram illustrating a top perspective view of a task cup configured to accommodate a suture training feature, as included in a complex surgical task portion shown in FIG. 10, by example only, in accordance with an embodiment of the present disclosure.

Still referring to FIG. 6B and referring back to FIG. 6A, the 2-D spiral training feature 128 and the 3-D spiral training feature 128' further provide training for: a second visuomotor task (point series) comprising touching a series of approximately eight (8) points with a tool having a pen tip, wherein a speed of execution is measured and recorded; a third visuomotor task (line/point series) comprising tracing a series of lines with the tool having the pen tip, wherein a speed of execution is measured and recorded, and wherein a demerit is assigned for each untouched dot disposed on the lines; a fourth visuomotor task (3D fidelity) comprising tracing two rows of five dots with the tool having the pen tip that scale the inside of the 3-D spiral training feature 128' (approximately 11 cm in height, approximately 9.5 cm, and approximately 5.2 cm in respective upper and base diameters), wherein the two rows of five dots are offset by approximately 2 cm from one another, and touching each of the dots from top to bottom of the 3-D spiral training feature 128', wherein a speed of execution is measured and recorded, and wherein a demerit is assigned for each untouched dot on each row; a fifth visuomotor task (3D line/point series) comprising sequentially touching "thumb" tags pressed on the 3-D spiral training feature 128', moving from the deepest region to the shallowest region thereof, wherein a speed of execution is measured and recorded; and an optional sixth visuomotor task comprising moving four items from one cup to another using Adson pickups and tying a knot around pillars with a suture string at the lowest point of the CST, e.g., at the complex surgical task portion 120, that accommodates a training feature comprising two cross pillars having an approximate 2 mm diameter and being disposed approximately 4 mm apart from one another, wherein a speed of execution is measured and recorded (FIG. 14).

Referring to FIG. 7, this diagram illustrates, in an exploded perspective view, a surgery simulator apparatus 100 of a multi-metric surgery simulator system S, operable with the enhanced simulated tissue products and methods, the surgery simulator apparatus 100 comprising at least one of a simple surgical task portion 110 and a complex surgical task portion 120, by example only, in accordance with an embodiment of the present disclosure. Each at least one surgery simulator apparatus 100 comprises at least one of a simple surgical task portion 110 and a complex surgical task portion 120; and each of the simple surgical task portion 110 and the complex surgical task portion 120 is configured to support training of the at least one surgical task in at least one of two dimensions and three dimensions. Each at least one surgery simulator apparatus 100 further comprises a housing 130 for accommodating at least one of the simple surgical task portion 110 and the complex surgical task portion 120.

Still referring to FIG. 7, the simple surgical task portion 110 comprises and/or accommodates simple surgical procedure training features for developing fundamental surgical gestures or psychomotor actions for handling simple surgical tasks that are prerequisite to developing a coordination level sufficiently high for handling complex tasks. Simple surgical tasks comprise any visuomotor skill task, such as 2-D tasks, e.g., spiral tracings for training gross navigation skills, line tracing for training fine navigation skills, and dot drawing for training fine target skills, placing pegs in holes, placing rings over pegs for handling general fine motor skills, and transferring small items between microsurgical instruments for handling fine coordination skills, by examples only.

Still referring to FIG. 7, the complex surgical task portion 120 comprises and/or accommodates complex surgical procedure training features for developing a coordination level for handling complex tasks, such as critical segments of a larger surgical procedure, e.g., having chronologically defined steps, wherein the complex surgical procedure training features simulate the surgical environment for the complex surgical procedure, and wherein the complex surgical tasks comprise a plurality of simple surgical tasks and/or a plurality of complex surgical tasks relating to the large surgical procedure, e.g., a brain tumour removal procedure. Complex surgical tasks also comprise any involved fine motor skill task, such as 3-D tasks, e.g., isolated knot-tying for training fine motor and coordination skills, simulated tumor removal for training resection skills, simulated aneurysm-clipping for training fine incision and suturing skills, simulated pedicle screw placement for training fine tapping, drilling, and turning skills, simulated spinal decompression with depth coloring features for training drilling, simulated inter-body fusion for training disk-fusing and the like, simulated fluid column use for verifying integrity of anastomosis or dural repair, by examples only.

Still referring to FIG. 7, each at least one surgery simulator apparatus 100 of a multi-metric surgery simulator system S further comprises at least one of: at least one simple surgical task portion fastener 111 for facilitating disposition of the at least one of the simple surgical task portion 110 in relation to the housing 130; at least one complex surgical task portion fastener 121 for facilitating disposition of the complex surgical task portion 120 in relation to the simple surgical task portion 110; and at least one housing fastener 131 for facilitating disposition of the housing 130 in relation to a generally horizontal surface (not shown), such as a workbench, laboratory bench, and a tabletop. The at least one surgery simulator apparatus 100 is configured to couple with the tracking feature 40, wherein the tracking feature 40 comprises at least one tracking marker 41, trackable by a tracking system.

Still referring to FIG. 7, the housing 130 comprises a generally angled frusto-conical configuration for facilitating simulation of a clinical access port environment. The at least one simple surgical task portion fastener 111 comprises at least one of at least one retention ring and any other suitable fastener. The at least one complex surgical task portion fastener 121 comprises at least one of at least one retention ring and any other suitable fastener. The at least one housing fastener 131 comprises at least one of a screw, a bolt, a nut, a threaded, a hook-and-loop fastener, and any other suitable fastener. The simple surgical task portion 110 comprises at least one of a generally conical configuration, a plurality of pin surgical task features 112, and a plurality of loop surgical task features 113. At least one of the plurality of pin surgical task features 112 and the plurality of loop surgical task features 113 is operatively coupled with the at least one sensor 10.

Referring to FIG. 8A, this diagram illustrates, in a side view, a surgery simulator apparatus 100 of a multi-metric surgery simulator system S, as shown in FIG. 7, operable with the enhanced simulated tissue products and methods, in accordance with an embodiment of the present disclosure. Each at least one surgery simulator apparatus 100 comprises at least one of a simple surgical task portion 110 and a complex surgical task portion 120; and each of the simple surgical task portion 110 and the complex surgical task portion 120 is configured to support training of the at least one surgical task in at least one of two dimensions and three dimensions. Each at least one surgery simulator apparatus 100 further comprises a housing 130 for accommodating at least one of the simple surgical task portion 110 and the complex surgical task portion 120. The system S further comprises a tracking apparatus 40 the tracking apparatus 40 comprising at least one tracking marker 41, such as at least one tracking sphere, by example only. The tracking apparatus 40 configured to track at least one tool used during training using the apparatus 100.

Referring to FIG. 8B, this diagram illustrates, in a front view, a surgery simulator apparatus 100 of a multi-metric surgery simulator system S, as shown in FIG. 7, operable with the enhanced simulated tissue products and methods, in accordance with an embodiment of the present disclosure. Each at least one surgery simulator apparatus 100 comprises at least one of a simple surgical task portion 110 and a complex surgical task portion 120; and each of the simple surgical task portion 110 and the complex surgical task portion 120 is configured to support training of the at least one surgical task in at least one of two dimensions and three dimensions. Each at least one surgery simulator apparatus 100 further comprises a housing 130 for accommodating at least one of the simple surgical task portion 110 and the complex surgical task portion 120. The system S further comprises a tracking apparatus 40, the tracking apparatus 40 comprising at least one tracking marker 41, such as at least one tracking sphere, by example only. The tracking apparatus 40 configured to track at least one tool used during training using the apparatus 100.

Referring to FIG. 9, this diagram illustrates, in a cross-sectional view, a surgery simulator apparatus 100 of a multi-metric surgery simulator system S, as shown in FIG. 7, operable with the enhanced simulated tissue products and methods, in accordance with an embodiment of the present disclosure. The plurality of pin surgical task features 112 comprises a plurality of pin holders 114 for accommodating a plurality of targets for facilitating training touching by at least one of at least one tool (not shown) and at least one instrument (not shown) in relation to the plurality of targets. The plurality of loop surgical task features 113 comprises a plurality of threaded eyebolts as guiding loops for facilitating training manipulation of at least one simulated elongated tissue feature therethrough.

Figure 10:
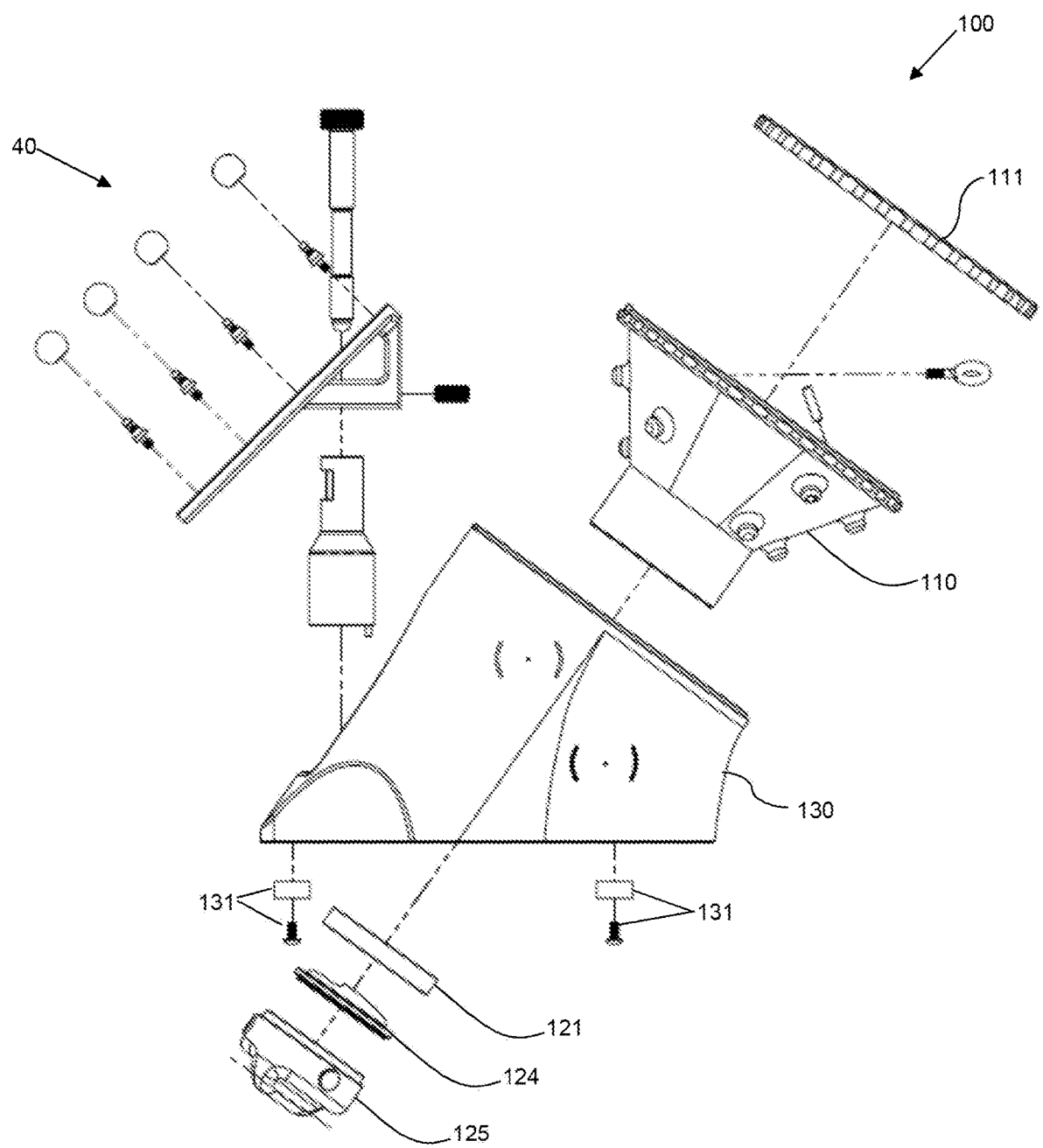
FIG. 10 is a diagram illustrating an exploded side view of a surgery simulator apparatus of a multi-metric surgery simulator system, the multi-metric surgery apparatus comprising at least one of a simple surgical task portion and a complex surgical task portion, in accordance with an embodiment of the present disclosure.

Referring to FIG. 10, this diagram illustrates, in an exploded side view, a surgery simulator apparatus 100 of a multi-metric surgery simulator system S, operable with the enhanced simulated tissue products and methods, the surgery simulator apparatus 100 comprising at least one of a simple surgical task portion 110 and a complex surgical task portion 120, in accordance with an embodiment of the present disclosure. The complex surgical task portion 120 comprises at least one of a generally cupped configuration, having a cap portion 124 and a cup portion 125, for facilitating simulation of a clinical subdural environment. The cup portion 125 accommodates the task cup 126. The cap portion 124 accommodates at least one simulated surface tissue feature (not shown) and facilitates training of the at least one surgical task in relation to the at least one simulated surface tissue feature (not shown). The cup portion 125 accommodates at least one simulated deep tissue feature (not shown) and facilitates training of the at least one surgical task in relation to the at least one simulated deep tissue feature (not shown).

Figure 11:
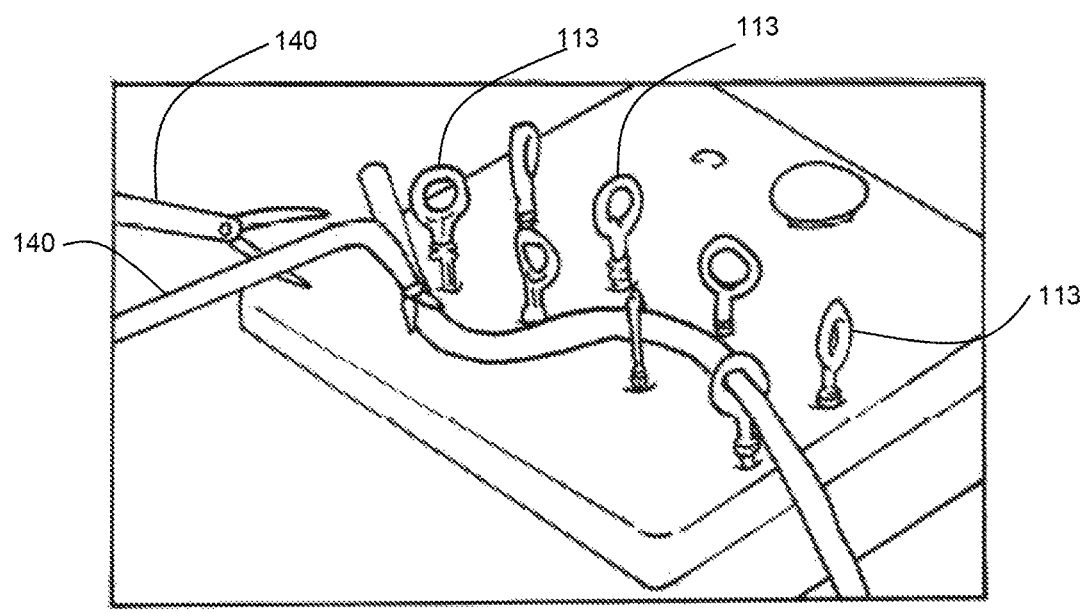
FIG. 11 is a diagram illustrating a top perspective view of a guide training feature having threaded eyebolts for guiding loops, as included in a simple surgical task portion shown in FIG. 10, by example only, in accordance with an embodiment of the present disclosure.

Referring to FIG. 11, is a diagram illustrating a top perspective view of a guide training feature having threaded eyebolts, such as plurality of loop surgical task features 113, as included in a simple surgical task portion shown in FIG. 10, by example only, operable with the enhanced simulated tissue products and methods, in accordance with an embodiment of the present disclosure. The plurality of loop surgical task features 113 comprises the plurality of threaded eyebolts as guiding loops for facilitating training manipulation of at least one simulated elongated tissue feature therethrough.

Figure 12:
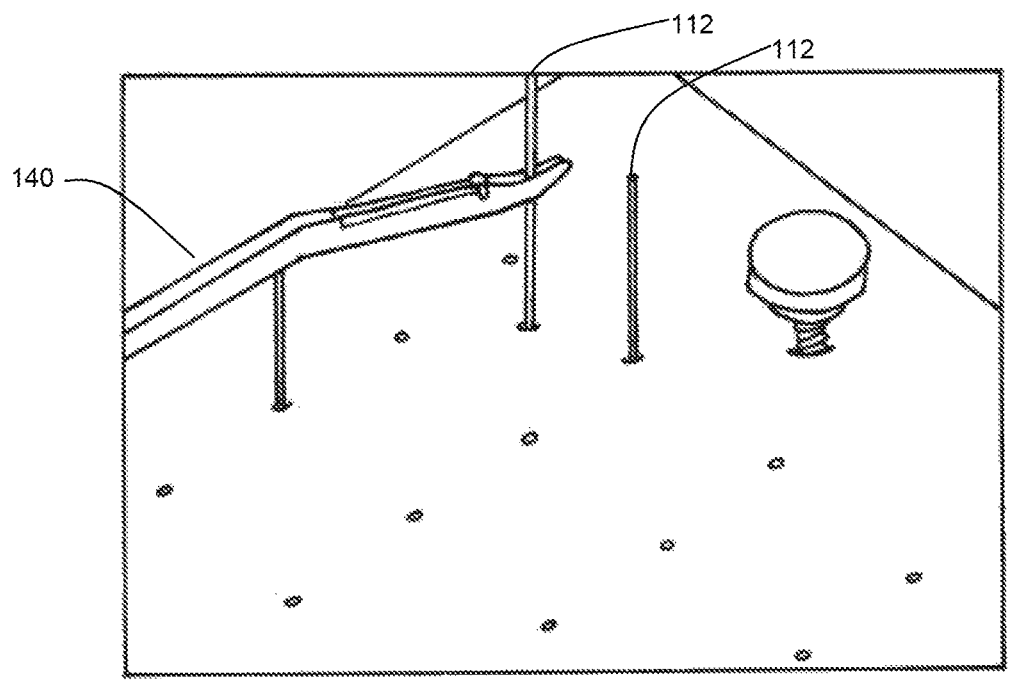
FIG. 12 is a diagram illustrating a top perspective view of a target training feature having pin holders, as included in a simple surgical task portion shown in FIG. 10, by example only, in accordance with an embodiment of the present disclosure.

Referring to FIG. 12, is a diagram illustrating a top perspective view of a target training feature having pin holders, as included in a simple surgical task portion shown in FIG. 10, by example only, operable with the enhanced simulated tissue products and methods, in accordance with an embodiment of the present disclosure. The plurality of pin surgical task features 112 comprises a plurality of pin holders 114 for accommodating a plurality of targets for facilitating training touching by at least one of at least one tool (not shown) and at least one instrument (not shown) in relation to the plurality of targets.

Figure 13:
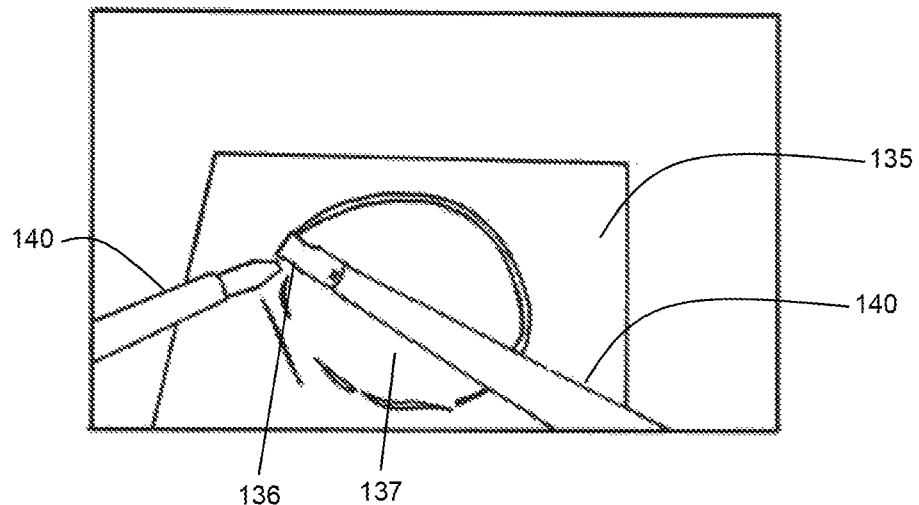
FIG. 13 is a diagram illustrating a top perspective view of an incision training feature, as included in a complex surgical task portion shown in FIG. 10, by example only, in accordance with an embodiment of the present disclosure.

Referring to FIG. 13, this diagram illustrates, in a top perspective view, an incision training feature 135 for facilitating training incising a bone cap and dura, as included in a complex surgical task portion 120 shown in FIG. 10, operable with the enhanced simulated tissue products and methods, by example only, in accordance with an embodiment of the present disclosure. The at least one simulated surface tissue feature 135 comprises at least one of a simulated epidermal tissue feature (not shown), a simulated dermal tissue feature (not shown), a simulated sub-dermal tissue feature (not shown), a simulated muscle tissue feature (not shown), a simulated cranial bone tissue feature 136, and a simulated dura tissue feature 137, by example only. At least one neurosurgical instrument 140, such as a scalpel, may be used for training incising the at least one simulated surface tissue feature 135. The simulated cranial bone tissue feature 136 comprises urethane or any material having properties that approximate that of natural bone, especially cranial tissue, by example only.

Still referring to FIG. 13, the incision training feature 135 facilitates training incising a bone cap and dura by providing training for approaching the surgical site, wherein training approaching comprises training commencing a craniotomy by forming a hole in a simulated cranium, thereby forming a cranial hole such as by forming a burr-hole, and a simulated bone portion, such as a simulated cranial flap, testing a range of motion of the port, and intra-operatively adjusting the simulated trajectory if required, forming an opening in a simulated dura, thereby forming a simulated dural flap, stitching-back the simulated dural flap, inserting the port, along the simulated trajectory via navigation guidance, such as provided on the at least one display device, and coaxially positioning a surgical camera, such as the optical camera of an CST feature, in relation to the port and the tracking feature 40.

Referring to FIG. 14, this diagram illustrates, in a top perspective view, a task cup 126 configured to accommodate a suture training feature 127 for facilitating training suturing, as included in a complex surgical task portion 120 shown in FIG. 10, by example only, operable with the enhanced simulated tissue products and methods, in accordance with an embodiment of the present disclosure. The complex surgical task portion 120 comprises at least one of a generally cupped configuration, having a cap portion 124 and a cup portion 125, for facilitating simulation of a clinical subdural environment. The cup portion 125 accommodates the task cup 126, wherein the task cup 126 further accommodates at least one simulated deep tissue feature (not shown), such as a simulated vascular tissue feature (not shown), a simulated neural tissue feature (not shown), and a simulated cerebral tissue feature (not shown). At least one neurosurgical instrument 140 may be used for training incising the suture training feature 127.

Referring to FIG. 15, this diagram illustrates, in a top view, a simple surgical task portion 110 comprising at least one of a 2-D spiral training feature 128 (FIGS. 6A and 6B) having at least one distinctive color-code feature 150, at least one measurement feature 151, guide training feature, such as the 2-D spiral training feature 128, and a target training feature 152 having at least one distinctive color-code feature 153, as included in a surgery simulator apparatus 100 of a multi-metric surgery simulator system S, operable with the enhanced simulated tissue products and methods, in accordance with an embodiment of the present disclosure. In this example, the simple surgical task portion 110 may also accommodate at least one representation of at least one simulated tissue structure having at least one of at least two dimensions, at least one color, and at least one pattern. The representation of at least one simulated tissue structure comprises at least one simulated tissue feature 135, wherein the at least one simulated tissue feature 135 comprises at least one of a simulated healthy tissue feature and a simulated pathological tissue feature. Laparoscopic training may be provided by way of a trainee touching the at least one distinctive color-code feature 153 using a pointer tool, a touch-pen, or a stylus (not shown). Such "touching" in terms of accuracy, pressure, and speed is measurable as part of the collected data 20, e.g., via the CST using the tacking apparatus 40 and effects an immediate response via the feedback 30 to the trainee.

Still referring to FIG. 15, at least one of the at least one surgical task pattern and the at least one simulated tissue feature 135 comprises at least one of a three-dimensional (3-D) color print and a surface-enhanced Raman Spectroscopy scattering material, wherein the surface-enhanced Raman Spectroscopy scattering material comprises a matrix material and a dopant, the matrix material comprising at least one of silicone and polyvinyl alcohol hydrogel, and the dopant comprising doped with at least one of a scattering agent, an absorption agent, and a calcification agent. The scattering agent comprises at least one of an intralipid and a nanoparticle. The absorption agent comprises an India ink. The calcification agent comprises calcium hydroxyapatite. The surface-enhanced Raman Spectroscopy scattering material is tunable in relation to at least one of at least one pathological tissue type, at least one pathological tissue mass, and at least one pathological tissue density for simulation thereof. The surface-enhanced Raman Spectroscopy scattering material comprises polyvinyl alcohol doped with at least one type of nanoparticle configured to simulate at least one of at least one disease state, at least one health condition, and the like. The simulator system S is configurable for use in virtual reality or augmented reality environments as well.

Still referring to FIG. 15, in accordance with the embodiments of the present disclosure, the systems and methods comprise simulated anatomical features also include negative (fluid-filled) spaces as sub-anatomy features in anatomical simulators/phantoms and utilize printing 3D structures using materials which are dissolvable once the simulator has been produced. In an embodiment of the present disclosure, a method of fabricating a simulated anatomical feature comprises steps, such as 3D printing of the negative space required, e.g., brain ventricles with a dissolvable material such as a PVA filament, to produce a printed 3D volume, and placing the printed 3D volume within a mold of an anatomical part, pouring a polyvinyl alcohol (PVA) formulation into a mold, thereby surrounding and encapsulating the printed 3D volume, exposing the encapsulated printed 3D volume to an appropriate number of freeze thaw cycles (FTC), thereby producing a tissue phantom with the desired biomechanical properties. The printed 3D volume is then dissolved, at least in part, to produce a fluid filled void having the approximate size and approximate shape of the printed 3D volume, e.g., in the undissolved state.

Still referring to FIG. 15, in accordance with the embodiments of the present disclosure, the filament material that is used to print the 3D volume is configured to result in a 3D volume capable of maintaining structural integrity through a plurality of FTCs and of complete dissolution for forming a negative space in the simulated tissue. The filament material comprises properties relating to a desired structural integrity. The filament material is also formable by printing the 3D volume and applying a protective layer of a water-resistant material to extend the filament material's life until the plurality of FTCs is complete.

Still referring to FIG. 15, in an embodiment of the present disclosure, a method of fabricating an anatomical feature that simulates the brain, the method comprises producing the ventricles and cerebral spinal fluid (CSF) by printing a PVA filament having a wall thicknesses, thereby providing a final solution having a targeted viscosity. This method ensures slowing the rate of equalization of concentrations of various materials, e.g., PVA and water, thereby preventing a change in shape of the structure or impinging on the shelf/usable life of the product. The method of fabricating an anatomical feature further comprises adding further materials, such as cornstarch, to a for facilitating water retention in the spaces, such as the ventricles and the spinal fluid areas.

Still referring to FIG. 15, in accordance with other embodiments of the present disclosure, the systems and methods comprise using alternative filaments, such as high impact polystyrene (HIPS) as a solute and limonene as dissolution agent. In accordance with other embodiments of the present disclosure, the systems and methods comprise using additives, such as salt, sugar, sand, and silicone may be used. In another embodiment, vascularity is presentable by 3D printing on a red plastic using a high resolution and PVA filament as scaffold, e.g., by placing the filament in a hydrogel contained in a silicone mold and immersing in the hydrogel formulation, thereby forming a simulator, optionally comprising a plurality of FTCs. The solution would dissolve the scaffold and form a cryogel supporting the printed structure.

Still referring to FIG. 15, in accordance with an embodiment of the present disclosure, a method of fabricating a simulated anatomical structure having at least one void comprises: 3D printing at least one simulated anatomical feature having at least one simulated sub-anatomical feature using a dissolvable material; supporting and enclosing the one or more structures in an interior of a mold of the anatomical phantom; filling a remaining internal volume in the interior of the mold between an outer surface of the one or more structures and an inner surface of the mold with a liquid precursor of a matrix material selected to mimic anatomical tissue and processing said liquid precursor to form a tissue mimic matrix material; and dissolving the one or more structures with a fluid selected to dissolve said dissolvable material to produce one or more internal cavities within the tissue mimic matrix material.

Still referring to FIG. 15, in accordance with an embodiment of the present disclosure, a method of fabricating a simulated void structure in a simulated anatomical structure comprises: printing, using 3D printing with silicone, one or more hollow structures of one or more desired sub-anatomical features, connecting the one or more hollow structures to a proximal end of an associated fluid flow channel; supporting and enclosing the one or more hollow structures and associated fluid flow channel in an interior of a mold of the anatomical phantom with a distal end of the associated fluid flow channel being located on an exterior of the mold; filling a remaining internal volume in the interior of the mold between an outer surface of both the one or more hollow structures and the associated vasculature and an inner surface of the mold with a liquid precursor of a matrix material selected to mimic anatomical tissue, the liquid precursor including at least polyvinyl alcohol, and curing the polyvinyl alcohol to produce a polyvinyl alcohol-based hydrogel to form a tissue mimic matrix material; and filling, through the access port, the one or more one hollow structures and their associated vasculature with liquid solutions selected to mimic preselected bodily fluids.

Referring to FIG. 16, this diagram illustrates, in a top view, a simple surgical task portion 110 comprising at least one of a 2-D spiral training feature 128 (FIGS. 6A and 6B) having a color-code feature 150, at least one measurement feature 151, guide training feature, such as the 2-D spiral training feature 128, and a target training feature 152 having a color-code feature 153, as (FIG. 15), as included in a surgery simulator apparatus 100 of a multi-metric surgery simulator system S, operable with the enhanced simulated tissue products and methods, in accordance with an embodiment of the present disclosure. The at least one measurement feature 151 comprises a linear feature 151a and a plurality of graduated indicia 151b, e.g., for indicating depth. Each graduated indicia 151b of the plurality of graduated indicia 151b, comprises numeral indicia 151c for indicating a surgical depth.

Referring to FIG. 17, this diagram illustrates, in an alternative cut-away interior perspective view, a simple surgical task portion 110 comprising at least one of a 2-D spiral training feature 128 (FIGS. 6A and 6B) having a color-code feature 150, at least one measurement feature 151, guide training feature, such as the 2-D spiral training feature 128, and a target training feature 152 having a color-code feature 153 (FIG. 15), as included in a surgery simulator apparatus 100 of a multi-metric surgery simulator system S, operable with the enhanced simulated tissue products and methods, in accordance with an embodiment of the present disclosure. The at least one measurement feature 151 comprises a linear feature 151a and a plurality of graduated indicia 151b, e.g., for indicating depth. Each graduated indicia 151b of the plurality of graduated indicia 151b, further comprises numeral indicia 151c for indicating a surgical depth.

Figure 18:
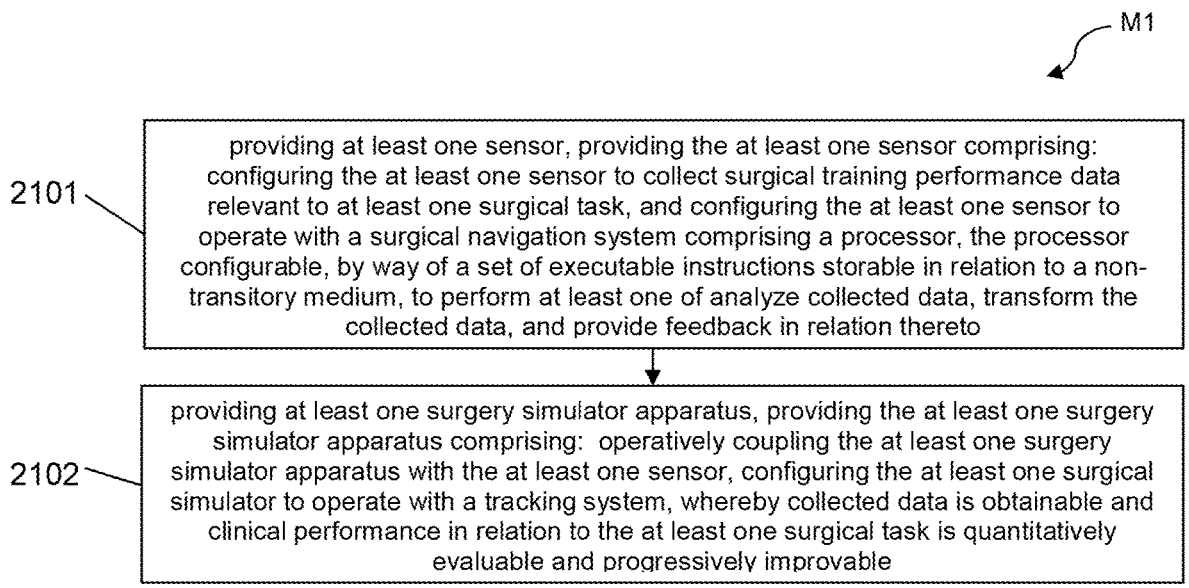
FIG. 18 is a flow diagram illustrating a method of fabricating a multi-metric surgery simulator system, in accordance with an embodiment of the present disclosure

Referring to FIG. 18, this flow diagram illustrates a method M1 of fabricating a multi-metric surgery simulator system S, operable with the enhanced simulated tissue products and methods, in accordance with an embodiment of the present disclosure. The method M1 comprises: providing at least one sensor, providing the at least one sensor comprising: configuring the at least one sensor to collect surgical training performance data relevant to at least one surgical task, and configuring the at least one sensor to operate with a surgical navigation system comprising a processor, the processor configurable, by way of a set of executable instructions storable in relation to a non-transitory medium, to perform at least one of analyze collected data, transform the collected data, and provide feedback in relation thereto, as indicated by block 2101; and providing at least one surgery simulator apparatus, providing the at least one surgery simulator apparatus comprising: operatively coupling the at least one surgery simulator apparatus with the at least one sensor, configuring the at least one surgical simulator to operate with a tracking system, whereby collected data is obtainable and clinical performance in relation to the at least one surgical task is quantitatively evaluable and progressively improvable, as indicated by block 2102.

Figure 19:
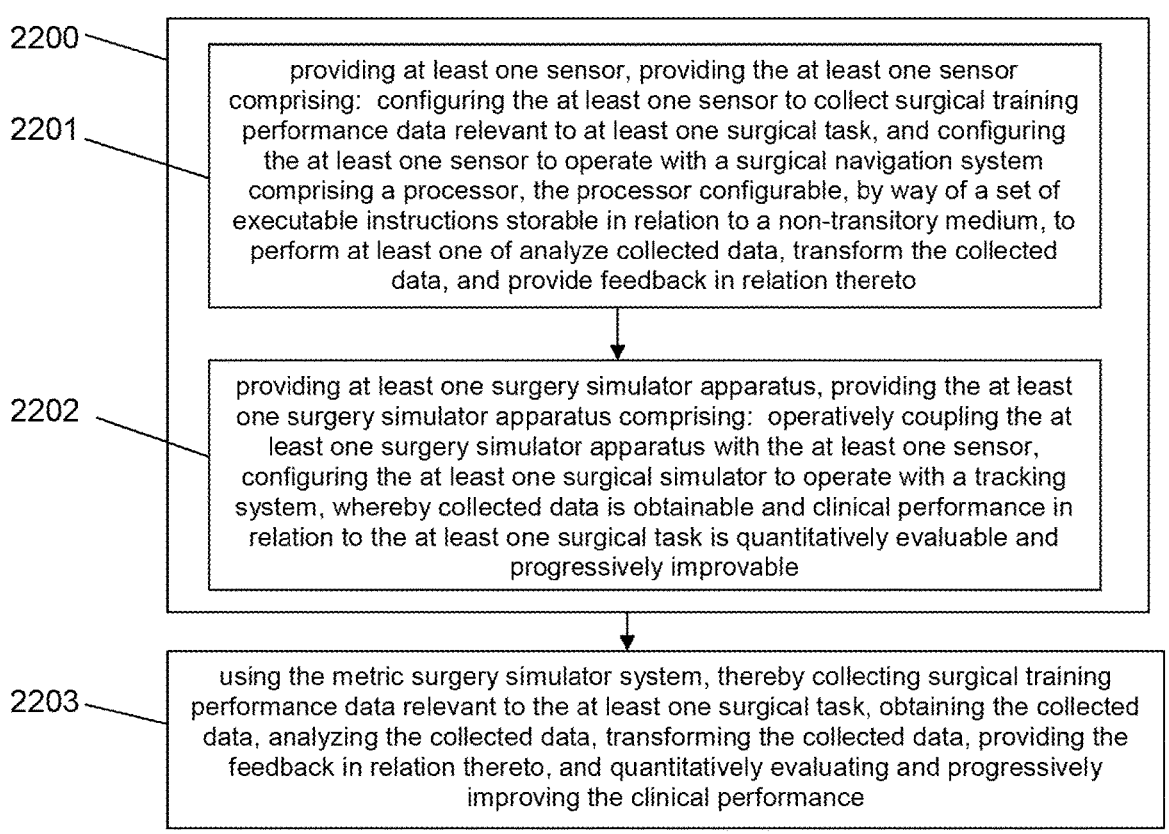
FIG. 19 is a flow diagram illustrating a method of quantitatively evaluating and progressively improving clinical performance of at least one surgical task by way of a multi-metric surgery simulator system, in accordance with an embodiment of the present disclosure.

Referring to FIG. 19, this flow diagram illustrates a method M2 of quantitatively evaluating and progressively improving clinical performance of at least one surgical task by way of a multi-metric surgery simulator system S, operable with the enhanced simulated tissue products and methods, in accordance with an embodiment of the present disclosure. The method M2 comprises: providing the multi-metric surgery simulator system S, as indicated by block 2200, providing the multi-metric surgery simulator system S comprising: providing at least one sensor 10, providing the at least one sensor 10 comprising: configuring the at least one sensor 10 to collect surgical training performance data relevant to at least one surgical task, and configuring the at least one sensor 10 to operate with a surgical navigation system comprising a processor, the processor configurable, by way of a set of executable instructions storable in relation to a non-transitory medium, to perform at least one of analyze collected data, transform the collected data, and provide feedback in relation thereto, as indicated by block 2201; and providing at least one surgery simulator apparatus 100, providing the at least one surgery simulator apparatus 100 comprising: operatively coupling the at least one surgery simulator apparatus 100 with the at least one sensor 10, configuring the at least one surgical simulator 100 to operate with a tracking system, whereby collected data 20 is obtainable and clinical performance in relation to the at least one surgical task is quantitatively evaluable and progressively improvable, as indicated by block 2202; and using the metric surgery simulator system S, thereby collecting surgical training performance data relevant to the at least one surgical task, obtaining the collected data 20, analyzing the collected data 20, transforming the collected data 20, providing the feedback 30 in relation thereto, and quantitatively evaluating and progressively improving the clinical performance, as indicated by block 2203. In the method M2, analyzing the collected data 20 comprises evaluating a trainee's current training session data in relation to at least one of initial threshold data relating to the surgical task, a trainee's past training session data, at least one other trainee's past training session data, and a historical average of at least one other trainee's past training session data.

Still referring to FIG. 19, transforming the collected data 20 in the method M2 comprises at least one of: iteratively determining new threshold data using at least one of the trainee's current training session data in relation to at least one of the initial threshold data relating to the surgical task, the trainee's past training session data, the at least one other trainee's past training session data, and the historical average of at least one other trainee's past training session data; and incorporating at least one social component into the new threshold data, the at least one social component comprising at least one of a competitive award, a competitive prize, and the like, thereby providing historical statistical data for use in self-reconfiguring the at least one surgery simulator apparatus 100 for optimizing quantitative evaluation and progressive improvement of clinical performance and for optimizing integration with at least one of a plurality of tools, a plurality of instruments, a plurality of tracking systems, and a plurality of navigation systems.

Referring back to FIGS. 1-19, embodiments of the system S may be implemented using at least one processor with, or without, additional instructions stored in a memory, e.g., for execution by at least one general purpose microprocessor. Thus, the present disclosure is not limited to any specific configuration of hardware, firmware, and/or software. While some embodiments of the present disclosure are implementable in fully functioning computers and computer systems, various embodiments are capable of being distributed as a computing product in a variety of forms and are capable of being applied, regardless of the particular type of machine or computer readable media used to actually effect the distribution of the various embodiments. At least some aspects disclosed can be embodied, at least in part, in software. That is, the techniques may be carried out in a computer system or other data processing system in response to a processor, such as a microprocessor, executing sequences of instructions contained in a memory, such as ROM, volatile RAM, non-volatile memory, cache, or a remote storage device. A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

Still referring back to FIGS. 1-19, the preceding example embodiments involve systems and methods in which a device is intra-operatively configured based on the identification of a medical instrument. In other example embodiments, one or more devices may be automatically controlled and/or configured by determining one or more context measures associated with a medical procedure. A "context measure", as used herein, refers to an identifier, data element, parameter or other form of information that pertains to the current state of a medical procedure. In one example, a context measure may describe, identify, or be associated with, the current phase or step of the medical procedure. In another example, a context measure may identity the medical procedure, or the type of medical procedure, that is being performed. In another example, a context measure may identify the presence of a tissue type, or a simulated tissue type, during a medical procedure, or a surgical training session. In another example, a context measure may identify the presence of one or more fluids, such as biological fluids, simulated biological fluids, or non-biological fluids, e.g. wash fluids, during the medical procedure, and may further identify the type of fluid. Each of these examples relate to the image-based identification of information pertaining to the context of the medical procedure or simulated medical procedure.

Still referring back to FIGS. 1-19, examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media, e.g., compact discs (CDs), digital versatile disks (DVDs), etc. The instructions can be embodied in digital and analog communication links for electrical, optical, acoustical, or other forms of propagated signals, such as carrier waves, infrared signals, digital signals, and the like. The storage medium may be the internet cloud, an informatics cloud server, or a computer readable storage medium such as a disc.

Still referring back to FIGS. 1-19, at least some of the methods described herein are capable of being distributed in a computer program product comprising a computer readable medium that bears computer usable instructions for execution by at least one processor to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Figure 20:
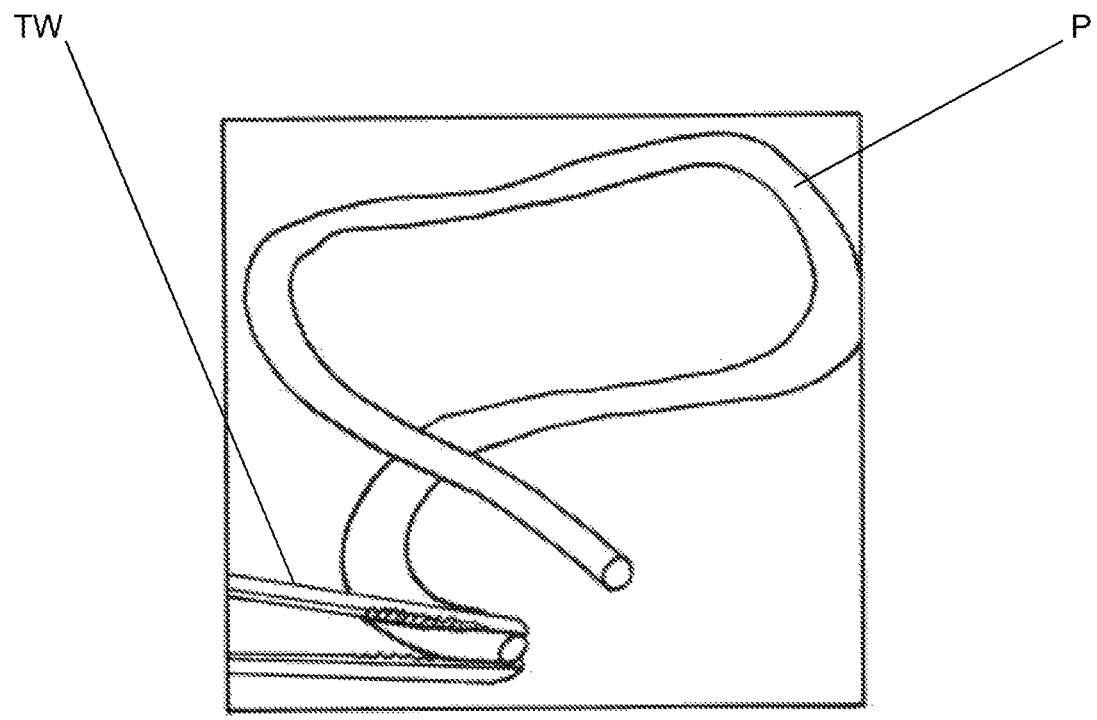
FIG. 20, is a diagram illustrating a top perspective view of an enhanced simulated tissue product, comprising a simulated blood vessel, by example only, and operable with the enhanced tissue products and methods, in accordance with an embodiment of the present disclosure.

Referring to FIG. 20, this diagrams illustrates, in a top perspective view, an enhanced simulated tissue product P comprising a simulated blood vessel, by example only, operable with a surgery simulator apparatus 100 of a multi-metric surgery simulator system S, in accordance with an embodiment of the present disclosure. The enhanced simulated tissue product P comprises: a polyvinyl alcohol material having a molecular chain length in a range of at least approximately 7000 vinyl alcohol repeat units; and water. In a preferred embodiment, the enhanced simulated tissue product comprises a polyvinyl alcohol material having a molecular chain length in a range of at least approximately 7150 vinyl alcohol repeat units, e.g., at least approximately 7150+/−100 vinyl alcohol repeat units, e.g., a higher molecular weight PVA than any related art formulation. In the formulations for the enhanced simulated tissue products P of the present disclosure, adverse fillers, such as silica particles, and adverse solvent, such as DMSO, are eliminated. The enhanced simulated tissue product P involves many embodiments, e.g., that simulate structures beyond vascularity, such as nerve bundles, and is configured to allow for testing standard surgical skills, facilitate training customization, and to provide consumable simulation products. The product P is capable of being manipulated by a variety of surgical training tools, such as tweezers TW, suturing needles, and the like.

Still referring to FIG. 20, the aqueous polyvinyl alcohol solution further comprises an additive, wherein the additive comprises a plurality of nanoparticles, and wherein the plurality of nanoparticles comprises at least one of at least one color representing at least one of healthy natural tissue, pathological natural tissue, a pathological material, a foreign material, and a contamination material; at least one diffusive property for enhancing imaging; and at least one mechanical property for at least one of resisting collapse, supporting suturing, and whereby the enhanced simulated tissue product is configurable for use with at least one system of a medical training system, a surgical training system, a surgery simulator system, a metric surgery simulator system, a medical navigation system, a medical tracking system, and an anastomosis system. The at least one color, representing the pathological tissue, comprises a color that represents a plaque material.

Figure 21:
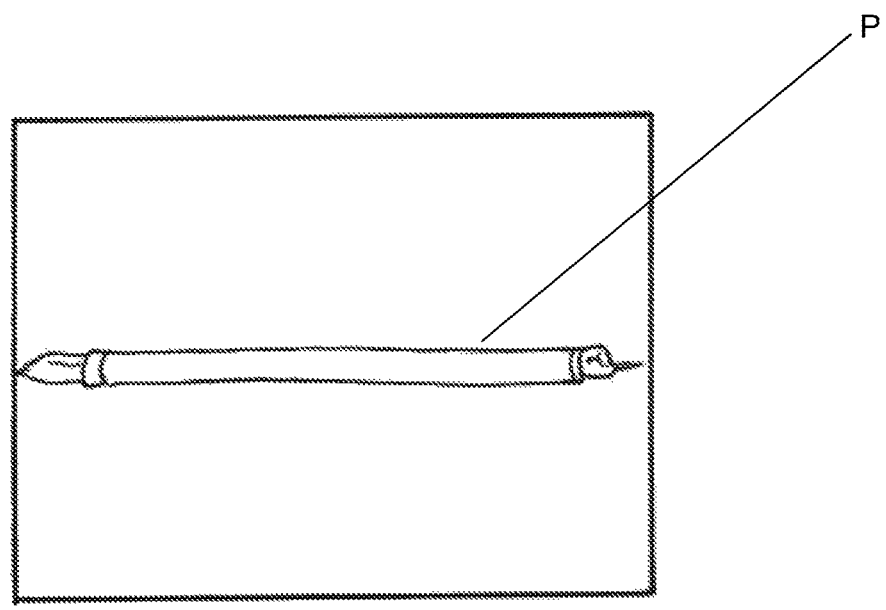
FIG. 21, is a diagram illustrating a top perspective view of an enhanced simulated tissue product, comprising a simulated nerve bundle, by example only, and operable with the enhanced tissue products and methods, in accordance with an embodiment of the present disclosure.

Referring to FIG. 21, referring back to FIG. 20, and referring ahead to FIGS. 22, 23A, and 23B, the product P, operable with a surgery simulator apparatus 100 of a multi-metric surgery simulator system S, further comprises an outer surface comprising a generally circular cross-section and at least one inner surface comprising at least one generally circular cross-section, e.g., having a lumen. The product P is configurable to approximate at least one of a natural blood vessel, a branch of natural blood vessels, a natural nerve bundle, and a branch of nerve bundles, wherein the product is resistant to collapse, and wherein the product is consumable. Additionally, the product P is configurable by way of a depression in the second mold member for forming additional features, such as representations (simulations) of plaque on an internal surface.

Referring to FIGS. 21A-21D, these diagrams illustrate various components of an CST for facilitating training at a plurality of different degrees of difficulty and a heightened level of realism in relation to performing an anastomosis task, in accordance with embodiments of the present disclosure. The CST comprises the following features: a feature for training at a plurality of different degrees of difficulty, a feature for customizing partially obscured viewing angles, a feature for simulating a corridor-type surgery requiring bayoneted instruments, a feature for customizing modules with realistic scenarios, such as simulating gyri and sulci, functional blood vessels, dura, and the like, a feature for testing standard visuomotor skills, a teaching platform for training of automated positioning systems, such as Drive™, and a teaching platform for training using optical systems, such as Vision™ Referring to FIG. 25A, this diagram illustrates, in a top view, a surgery simulator apparatus 100, as shown in FIGS. 7-10, comprising in accordance with an embodiment of the present disclosure.

Referring to FIG. 21A, this diagram illustrates, in a top view, a surgery simulator apparatus 100, as shown in FIGS. 7-10, comprising a simple surgical task portion 110 having a simple surgical task portion fastener 111 and complex surgical task portion 120, operable with the enhanced products and methods, in accordance with an embodiment of the present disclosure.

Referring to FIG. 21B, this diagram illustrates, in a top view, a surgery simulator apparatus 100, as shown in FIGS. 7-10, comprising a simple surgical task portion 110 having a simple surgical task portion fastener 111 (removed to better illustrate internal components) and complex surgical task portion 120, operable with the enhanced products and methods, in accordance with an embodiment of the present disclosure.

Referring to FIG. 21C, this diagram illustrates, in a side view, a surgery simulator apparatus 100, as shown in FIGS. 7-10, comprising a simple surgical task portion 110 having a simple surgical task portion fastener 111 and complex surgical task portion 120, operable with the enhanced products and methods, in accordance with an embodiment of the present disclosure.

Referring to FIG. 21D, this diagram illustrates, in a side view, a surgery simulator apparatus 100, as shown in FIGS.

7-10, comprising a simple surgical task portion 110 having a simple surgical task portion fastener 111 (removed to better illustrate internal components) and complex surgical task portion 120, disassembled, operable with the enhanced products and methods, in accordance with an embodiment of the present disclosure.

Referring to FIG. 22, this diagram illustrates, in a side internal perspective view, two conditions relating to vascular health, such as in relation to a human leg, by example only, the two conditions comprising a normal artery condition (cut-away view) and a narrowed atherosclerotic arterial condition (cut-away view), wherein the product P is configurable to represent these two conditions for facilitating surgical training, such as for procedures for arterial treatments, e.g., ultrasonic techniques, blood vessel grafting, stent inserting, and the like, operable with a surgery simulator apparatus 100 of a multi-metric surgery simulator system S, as shown in FIGS. 7-10, comprising a simple surgical task portion 110 having a simple surgical task portion fastener 111 (removed to better illustrate internal components) and a complex surgical task portion 120, disassembled, in accordance with an embodiment of the present disclosure.

Referring to FIG. 23A, this diagram illustrates, in a cut-away perspective view, a condition relating to vascular health, such as in relation to a human leg, by example only, the condition comprising a normal artery condition (cut-away view), wherein the product P is configurable to represent such condition for facilitating surgical training, such as for identifying healthy tissue, the product P, operable with a surgery simulator apparatus 100 of a multi-metric surgery simulator system S, as shown in FIGS. 7-10, comprising a simple surgical task portion 110 and a complex surgical task portion 120, disassembled, in accordance with an embodiment of the present disclosure.

Referring to FIG. 23B, this diagram illustrates, in a cut-away perspective view, a condition relating to vascular health, such as in relation to a human leg, by example only, the condition comprising a narrowed atherosclerotic arterial condition (cut-away view), wherein the product P is configurable to represent such condition for facilitating surgical training, such as for identifying pathological tissue, the product P, operable with a surgery simulator apparatus 100 of a multi-metric surgery simulator system S, as shown in FIGS. 7-10, comprising a simple surgical task portion 110 and a complex surgical task portion 120, disassembled, in accordance with an embodiment of the present disclosure.

Referring to FIG. 24, this flow diagram illustrates a method M3 of fabricating an enhanced simulated tissue product P, operable with a surgery simulator apparatus 100 of a multi-metric surgery simulator system S, the method M3 comprising: providing an aqueous polyvinyl alcohol solution, as indicated by block 2800, providing the aqueous polyvinyl alcohol solution, as indicated by block 2800, comprising providing a polyvinyl alcohol material having a molecular chain length in a range of at least approximately 7000 vinyl alcohol repeat units, as indicated by block 2801, providing water, as indicated by block 2802, and dissolving the polyvinyl alcohol material in the water, as indicated by block 2803; molding the aqueous polyvinyl alcohol solution, as indicated by block 2804; and iteratively temperature-cycling the aqueous polyvinyl alcohol solution, as indicated by block 2805, thereby providing the enhanced simulated tissue product, in accordance with an embodiment of the present disclosure.

Still referring to FIG. 24, in the method M3, providing the aqueous polyvinyl alcohol solution comprises providing a polyvinyl alcohol material having a molecular chain length in a range of at least approximately 7150 vinyl alcohol repeat units, e.g., at least approximately 7150+/−100 vinyl alcohol repeat units, providing the aqueous polyvinyl alcohol solution comprises providing polyvinyl alcohol in a preferred concentration of approximately 10% weight in water, providing the aqueous polyvinyl alcohol solution further comprises providing an additive, providing the additive comprises providing a plurality of nanoparticles.

Still referring to FIG. 24, in the method M3, providing the plurality of nanoparticles comprises at least one of: providing at least one color associated with at least one of healthy natural tissue, pathological natural tissue, a pathological material, a foreign material, and a contamination material; providing at least one diffusive property for enhancing imaging; and providing at least one mechanical property for at least one of resisting collapse and supporting suturing, whereby the enhanced simulated tissue product is configured for use with at least one system of a medical training system, a surgical training system, a surgery simulator system, a metric surgery simulator system, a medical navigation system, a medical tracking system, and an anastomosis system.

Still referring to FIG. 24, in the method M3, providing the at least one color, representing the pathological tissue, comprises providing a color that represents a plaque material, molding comprises at least one technique of casting, injection molding, vacuum molding, compression molding, extrusion molding, matrix molding, rotational molding, and thermoforming. Molding comprises providing a plurality of mold portions, providing the plurality of mold portions comprises: providing an outer mold portion; and providing at least one inner mold portion.

Still referring to FIG. 24, in the method M3, providing the outer mold portion comprises configuring the outer mold portion to accommodate the at least one inner mold portion, providing the outer mold portion comprises configuring the outer mold portion to complementarily simulate an outer surface of natural tissue, providing the at least one inner mold portion comprises configuring the inner mold portion to complementarily simulate an inner surface of the natural tissue, whereby the enhanced simulated tissue product comprises physical properties that approximate the natural tissue. An enhanced simulated tissue product P fabricated by the method M3 is encompassed by the present disclosure as well.

Still referring to FIG. 24, in the method M3, at least one of: providing the outer mold portion comprises configuring the outer mold with a generally circular cross-section; and providing the at least one inner mold portion comprises configuring the inner mold with a generally circular cross-section, whereby the enhanced simulated tissue product comprises at least one configuration approximating a natural blood vessel, a branch of natural blood vessels, a natural nerve bundle, and a branch of nerve bundles, whereby the enhanced simulated tissue product is resistant to collapse, and whereby the product is consumable.

Still referring to FIG. 24, in the method M3, iteratively temperature-cycling comprises: freezing the aqueous polyvinyl alcohol solution; and thawing the aqueous polyvinyl alcohol solution, wherein freezing comprises subjecting the aqueous polyvinyl alcohol solution to a temperature in a range of approximately −10° C. and less, wherein thawing comprises subjecting the aqueous polyvinyl alcohol solution to a temperature in a range of approximately 20° C. and more, wherein thawing comprises slowly thawing the aqueous polyvinyl alcohol solution by way of refrigeration from a temperature in a range of approximately −11° C. to approximately +10° C. in a duration range of approximately 3 hours to approximately 12 hours, depending on the need, e.g., for a simulated blood vessel. The temperature at a thawed state comprises an ambient temperature of a chamber or a room. For a simulated brain tissue, the duration range is slower than that for the simulated blood vessel, e.g., a duration in a range of approximately 12 hours to approximately 24 hours. Alternatively, iteratively temperature-cycling comprises: cooling the aqueous polyvinyl alcohol solution to a temperature in a range of at least less than approximately freezing; holding freezing the aqueous polyvinyl alcohol solution at a temperature in the range of at least less than approximately freezing; thawing the aqueous polyvinyl alcohol solution to a temperature in a range of at least greater than ambient; and holding thawing the aqueous polyvinyl alcohol solution at a temperature range of at least greater than ambient Still referring to FIG. 24, in the method M3, molding the aqueous polyvinyl alcohol solution, as indicated by block 2804, comprises providing a mold arrangement, providing the mold arrangement comprises providing a first mold member comprising an inner dimension, such as an inner diameter, at least approximating an outer dimension, such as an outer diameter, of an anatomical structure, such as a blood vessel, and providing a second mold member comprising an outer dimension, such as an outer diameter, at least approximating an inner dimension, such as an inner diameter, of the anatomical structure, such as the blood vessel, wherein the second mold member is disposable within at least a portion of the first mold member, e.g., for facilitating extrusion of the aqueous polyvinyl alcohol solution therebetween.

Still referring to FIG. 24, in the method M3, providing water, as indicated by block 2802, comprises providing water in a range of approximately 7 weight % to approximately 10 weight %, molding the aqueous polyvinyl alcohol solution, as indicated by block 2804, further comprises filling a cavity between the first and second mold members with the aqueous polyvinyl alcohol solution, and iteratively temperature-cycling the aqueous polyvinyl alcohol solution, as indicated by block 2805, comprises freezing the aqueous polyvinyl alcohol solution at a temperature in a range of up to approximately −11° C. and thawing the aqueous polyvinyl alcohol solution in at least one manner of thawing the aqueous polyvinyl alcohol solution in a temperature range up to approximately room temperature and, preferably, thawing the aqueous polyvinyl alcohol solution by refrigerating the aqueous polyvinyl alcohol solution within a temperature range of refrigeration, whereby the aqueous polyvinyl alcohol solution transitions into a gel, and whereby the product comprises the gel.

Still referring to FIG. 24, the method M3 further comprises removing the first and second mold members from the gel, whereby the gel is configured as a simulated anatomical structure, such as a blood vessel having thin walls and accurate, realistic, physical properties, wherein the simulated anatomical structure is configured to remain in an "expanded" disposition having a generally circular cross-section in the present of a fluid environment, and wherein the simulated anatomical structure is configured to collapse when the fluid environment is removed, thereby realistically simulating a broken blood vessel condition. In the method M3, providing an aqueous polyvinyl alcohol solution, as indicated by block 2800, further comprises providing a plurality of nanoparticles for imparting a desired colour corresponding to at least one of healthy tissue and pathological tissue and admixing the plurality of nanoparticles to at least one of the polyvinyl alcohol material and the water, wherein the plurality of nanoparticles comprise a plurality of colours corresponding to at least one of healthy tissue and pathological vessel.

Still referring to FIG. 24, by using the method M3, the product P comprises a simulated anatomical structure that is further configured to accept and hold sutures and is operable with a multi-metric system S, e.g., as a consumable training object. By using the method M3, simulated anatomical structure is alternatively configurable as a sheath, wherein bi-component fibers, such as used in a diffusion "phantom," is insertable through the sheath to form a simulated nerve bundle, thereby demonstrating diffusion during MR scans, and whereby the simulated nerve bundle is disposable in a task trainer (FIG. 21). By using the method M3, simulated anatomical structure is alternatively configurable as a complex anatomical structure, such as a branched structure, e.g., a neural network, a vascular network, an aneurysm, and other branched pathology structures, such as metastasized tumours.

Figure 25:
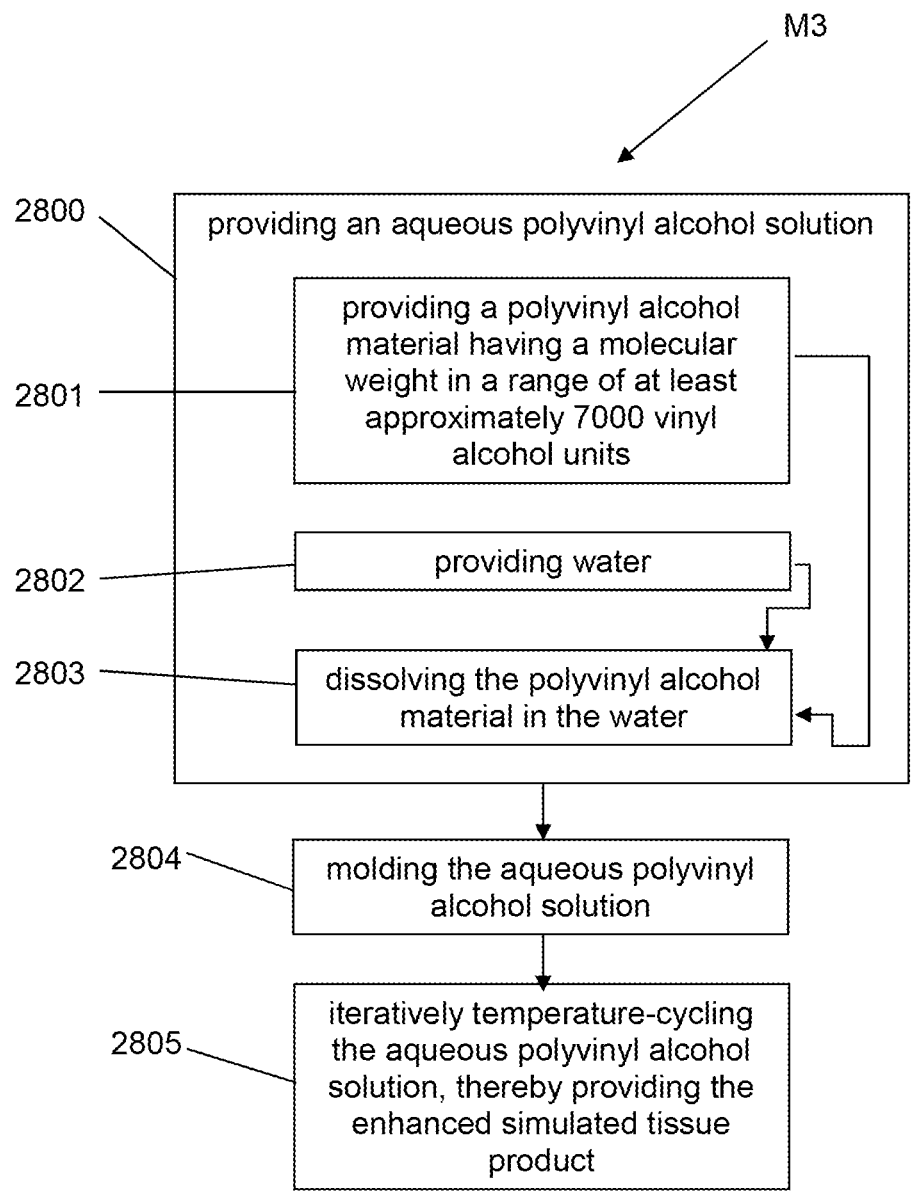
FIG. 25 is a flow diagram illustrating a method of fabricating an enhanced simulated tissue product, operable with a surgery simulator apparatus of a multi-metric surgical simulator system, a in accordance with an embodiment of the present disclosure.
Figure 26:
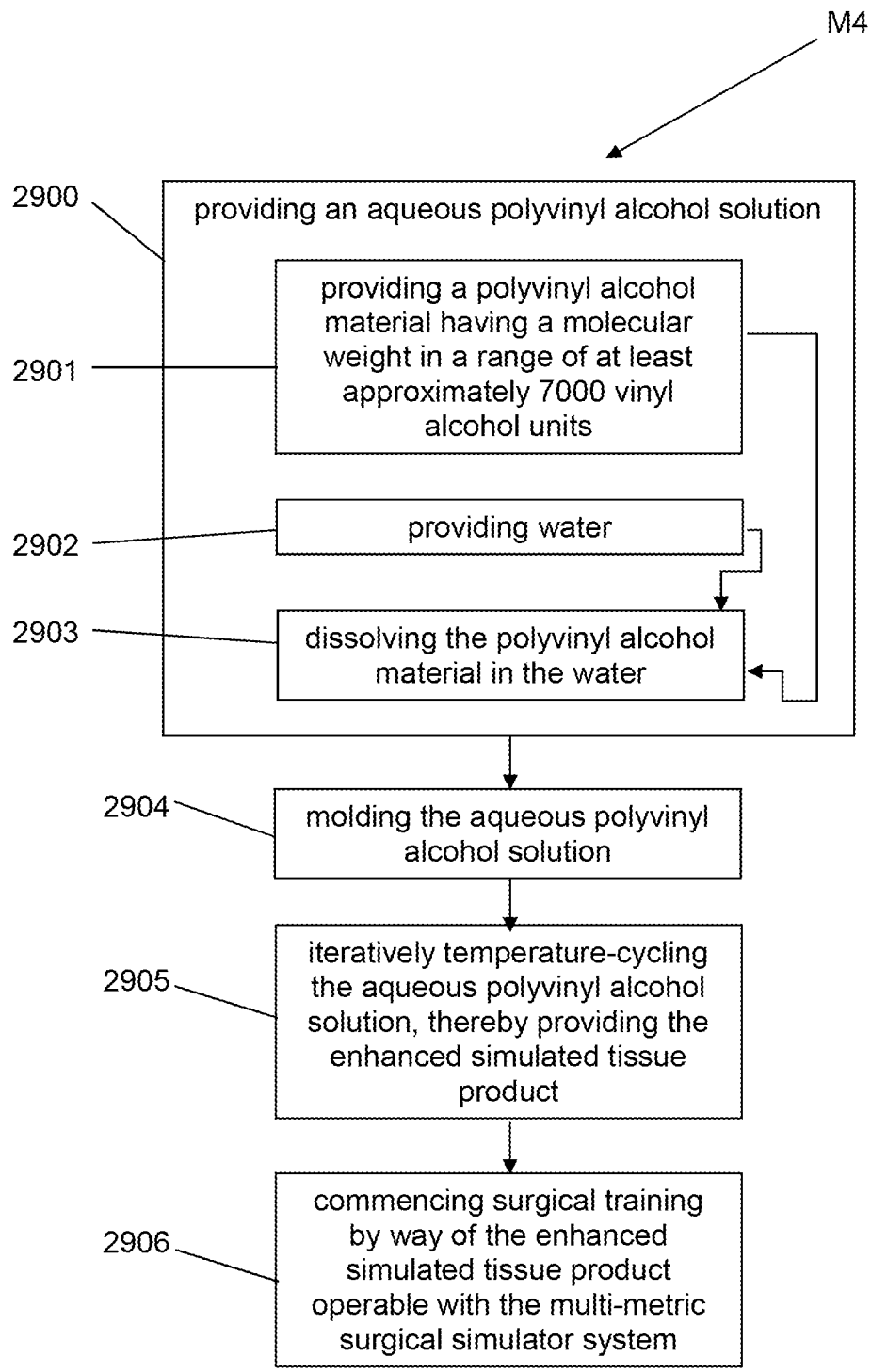
FIG. 26 is a flow diagram illustrating a method of using an enhanced simulated tissue product, e.g., with a surgery simulator apparatus of a multi-metric surgical simulator system, in accordance with an embodiment of the present disclosure.

Referring to FIG. 25, this flow diagram illustrates a method M4 of using an enhanced simulated tissue product, e.g., with a surgery simulator apparatus 100 of a multi-metric surgery simulator system S, comprises: providing the enhanced simulated tissue product P, providing the enhanced simulated tissue product P comprising providing an aqueous polyvinyl alcohol solution, as indicated by block 2900, providing the aqueous polyvinyl alcohol solution, as indicated by block 2900, comprising providing a polyvinyl alcohol material having a molecular chain length in a range of of at least approximately 7000 vinyl alcohol repeat units, as indicated by block 2901, providing water, as indicated by block 2902, and dissolving the polyvinyl alcohol material in the water, as indicated by block 2903; molding the aqueous polyvinyl alcohol solution, as indicated by block 2904; and iteratively temperature-cycling the aqueous polyvinyl alcohol solution, as indicated by block 2905, thereby providing the enhanced simulated tissue product; and commencing surgical training by way of the enhanced simulated tissue product operable with the multi-metric surgical simulator system, as indicated by block 2906, in accordance with an embodiment of the present disclosure.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

The subject matter of the present disclosure industrially applies to the field of tissue simulations for surgery simulators. More particularly, the subject matter of the present disclosure industrially applies to the field of tissue simulations for surgery simulators in relation to image guided medical procedures. Even more particularly, the subject matter of the present disclosure industrially applies to the field of tissue simulations for surgery simulators in relation to image guided medical procedures with surgical navigation.

What is claimed:

1. A method of fabricating an enhanced simulated tissue product, comprising:
    providing an aqueous polyvinyl alcohol solution, providing the aqueous polyvinyl alcohol solution comprising providing a polyvinyl alcohol material having a molecular chain length in a range of at least approximately 7000 vinyl alcohol repeat units, providing water, and dissolving the polyvinyl alcohol material in the water,
    wherein providing the aqueous polyvinyl alcohol solution comprises providing polyvinyl alcohol in a preferred concentration of approximately 10 weight % in water,
    wherein providing the aqueous polyvinyl alcohol solution further comprises providing an additive,
    wherein providing the additive comprises providing a plurality of nanoparticles, and
    wherein providing the plurality of nanoparticles comprises providing at least one portion thereof with at least one optically diffusive property for enhancing imaging and a surfaced-enhanced Raman scattering property;
    forming at least one simulated anatomical feature by 3D printing;
    molding the aqueous polyvinyl alcohol solution over the at least one simulated anatomical feature, thereby encapsulating the at least one simulated anatomical feature; and
    iteratively temperature-cycling the aqueous polyvinyl alcohol solution,
    thereby providing the enhanced simulated tissue product.

2. The method of claim 1, wherein providing the aqueous polyvinyl alcohol solution comprises providing the polyvinyl alcohol material having a molecular chain length in a range of at least approximately 7150 vinyl alcohol repeat units.

3. The method of claim 1, wherein molding comprises at least one technique of casting, injection molding, vacuum molding, compression molding, extrusion molding, matrix molding, rotational molding, and thermoforming.

4. The method of claim 1, wherein molding comprises providing a plurality of mold portions.

5. The method of claim 4, wherein providing the plurality of mold portions comprises:
    providing an outer mold portion; and
    providing at least one inner mold portion.

6. The method of claim 5,
    wherein providing the outer mold portion comprises configuring the outer mold portion to accommodate the at least one inner mold portion,
    wherein providing the outer mold portion comprises configuring the outer mold portion to complementarily simulate an outer surface of natural tissue,
    wherein providing the at least one inner mold portion comprises configuring each at least one inner mold portion to complementarily simulate an inner surface of the natural tissue, and
    whereby the enhanced simulated tissue product comprises physical properties that approximate the natural tissue.

7. The method of claim 5, wherein at least one of:
    providing the outer mold portion comprises configuring the outer mold portion with a generally circular cross-section; and
    providing the at least one inner mold portion comprises configuring each at least one inner mold with a generally circular cross-section,
    whereby the enhanced simulated tissue product comprises at least one configuration approximating a natural blood vessel, a branch of natural blood vessels, a natural nerve bundle, and a branch of nerve bundles,
    whereby the enhanced simulated tissue product is resistant to collapse, and
    whereby the product is consumable.

8. The method of claim 1, wherein iteratively temperature-cycling comprises:
    cooling the aqueous polyvinyl alcohol solution to a temperature in a range of at least less than approximately freezing;
    holding freezing the aqueous polyvinyl alcohol solution at a temperature in the range of at least less than approximately freezing;
    thawing the aqueous polyvinyl alcohol solution to a temperature in a range of at least greater than ambient; and
    holding thawing the aqueous polyvinyl alcohol solution at a temperature range of at least greater than ambient.

9. The method of claim 8,
    wherein cooling comprises freezing the aqueous polyvinyl alcohol solution to a temperature in a range of approximately −11° C. and less,
    wherein holding freezing comprises subjecting the aqueous polyvinyl alcohol solution to a temperature in a range of approximately −11° C. and less for a duration of approximately 14 hours,
    wherein thawing comprises subjecting the aqueous polyvinyl alcohol solution to a temperature in a range of approximately +10° C. and more for a duration of approximately 3 hours, and
    wherein holding thawing comprises subjecting the aqueous polyvinyl alcohol solution to 10 a temperature in a range of approximately +10° C. and more for a duration of approximately 6 hours.

10. The method of claim 8, wherein thawing comprises slowly thawing the aqueous polyvinyl alcohol solution by way of refrigeration from a temperature in a range of approximately −11° C. to approximately +10° C. in a duration range of approximately 3 hours to approximately 12 hours.

11. An enhanced simulated tissue product fabricated by the method of claim 1.

12. The method of claim 1,
wherein providing the at least one simulated anatomical feature comprises providing at least one of: a negative space, a simulated brain ventricle, a simulated vascular structure, and a simulated cerebral spinal fluid,
wherein providing the simulated cerebral spinal fluid is formed by at least partially dissolving a printed 3D volume, thereby forming a fluid-filled void,
wherein 3D printing comprises using at least one of a salt, a sugar, a corn starch, a sand, a silicone, and a combination of a polystyrene as a solute and a limonene as dissolution agent, and
wherein providing the simulated vascular structure comprises 3D printing a polyvinyl alcohol filament having a wall thicknesses.

13. A method of using an enhanced simulated tissue product operable with a multi-metric surgical simulator system, the method comprising:
providing the enhanced simulated tissue product operable with the multi-metric surgical simulator system, providing the enhanced simulated tissue product comprising providing an aqueous polyvinyl alcohol solution, providing the aqueous polyvinyl alcohol solution comprising providing a polyvinyl alcohol material having a molecular chain length in a range of at least approximately 7000 vinyl alcohol repeat units, providing water, and dissolving the polyvinyl alcohol material in the water,
wherein providing the aqueous polyvinyl alcohol solution comprises providing polyvinyl alcohol in a preferred concentration of approximately 10 weight % in water,
wherein providing the aqueous polyvinyl alcohol solution further comprises providing an additive,
wherein providing the additive comprises providing a plurality of nanoparticles, and
wherein providing the plurality of nanoparticles comprises providing at least one portion thereof with at least one optically diffusive property for enhancing imaging and a surfaced-enhanced Raman scattering property;
forming at least one simulated anatomical feature by 3D printing;
molding the aqueous polyvinyl alcohol solution over the at least one simulated anatomical feature, thereby encapsulating the at least one simulated anatomical feature;
iteratively temperature-cycling the aqueous polyvinyl alcohol solution,
thereby providing the enhanced simulated tissue product; and
commencing surgical training by way of the enhanced simulated tissue product.

14. The method of claim 13, wherein providing the aqueous polyvinyl alcohol solution comprises providing the polyvinyl alcohol material having a molecular chain length in a range of at least approximately 7150 vinyl alcohol repeat units.

15. The method of claim 13,
wherein iteratively temperature-cycling comprises:
cooling the aqueous polyvinyl alcohol solution to a temperature in a range of at least less than approximately freezing;
holding freezing the aqueous polyvinyl alcohol solution at a temperature in the range of at least less than approximately freezing;
thawing the aqueous polyvinyl alcohol solution to a temperature in a range of at least greater than ambient; and
holding thawing the aqueous polyvinyl alcohol solution at a temperature range of at least greater than ambient.

16. The method of claim 13,
wherein cooling comprises freezing the aqueous polyvinyl alcohol solution to a temperature in a range of approximately −11° C. and less,
wherein holding freezing comprises subjecting the aqueous polyvinyl alcohol solution to a temperature in a range of approximately −11° C. and less for a duration of approximately 14 hours,
wherein thawing comprises subjecting the aqueous polyvinyl alcohol solution to a temperature in a range of approximately +10° C. and more for a duration of approximately 3 hours,
wherein holding thawing comprises subjecting the aqueous polyvinyl alcohol solution to 10 a temperature in a range of approximately +10° C. and more for a duration of approximately 6 hours, and
wherein thawing comprises slowly thawing the aqueous polyvinyl alcohol solution by way of refrigeration from a temperature in a range of approximately −11° C. to approximately +10° C. in a duration range of approximately 3 hours to approximately 12 hours.

* * * * *